(12) United States Patent
Igov et al.

(10) Patent No.: US 10,582,940 B2
(45) Date of Patent: Mar. 10, 2020

(54) RIGID AND FLEXIBLE LAPAROSCOPIC TOOL SHAFTS AND METHODS USING SAME

(71) Applicant: TELEFLEX MEDICAL INCORPORATED, Research Triangle Park, NC (US)

(72) Inventors: Igor Igov, Lod (IL); Jonatan Epstein, Ramat-HaSharon (IL); Rami Lore, Kiryat-Tivon (IL); Gilad Lavi, Rishon-LeZion (IL)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 325 days.

(21) Appl. No.: 14/155,953

(22) Filed: Jan. 15, 2014

(65) Prior Publication Data

US 2014/0200610 A1    Jul. 17, 2014

Related U.S. Application Data

(60) Provisional application No. 61/753,224, filed on Jan. 16, 2013.

(51) Int. Cl.
*A61B 17/29* (2006.01)
*A61B 18/14* (2006.01)
*A61B 17/00* (2006.01)

(52) U.S. Cl.
CPC ................. *A61B 17/2909* (2013.01)

(58) Field of Classification Search
CPC ............ A61B 17/29; A61B 17/2909; A61B 2017/2901; A61B 2017/291; A61B 2017/2902; A61B 2017/2904; A61B 2017/2923; A61B 2017/00407; A61B 2017/2908; A61B 18/1482; A61B 2017/2912; A61B 2017/2909; A61B 2017/2837; A61B 17/00234; A61F 2/95; A61F 2002/9517
USPC .................................. 606/205–208
See application file for complete search history.

(56) References Cited

U.S. PATENT DOCUMENTS

| | | | |
|---|---|---|---|
| 4,043,323 A * | 8/1977 | Komiya | A61B 1/018 600/104 |
| 5,370,659 A | 12/1994 | Sakashita | |
| 5,741,285 A * | 4/1998 | McBrayer | A61B 17/29 606/170 |

(Continued)

FOREIGN PATENT DOCUMENTS

| | | |
|---|---|---|
| JP | 6-7366 A | 1/1994 |
| JP | 10503406 A | 3/1998 |

(Continued)

OTHER PUBLICATIONS

International Search Reported dated Mar. 21, 2014.

*Primary Examiner* — Diane D Yabut
*Assistant Examiner* — Majid Jamialahmadi
(74) *Attorney, Agent, or Firm* — Baker & Hostetler LLP

(57) ABSTRACT

Laparoscopic tool shafts and devices and methods for enhancing their rigidity in general or in specific directions are provided. Laparoscopic tool shafts having rigid external shafts and relatively rigid rods and laparoscopic tool shafts having flexible external shafts and relatively rigid rods are also provided.

12 Claims, 34 Drawing Sheets

(56) References Cited

U.S. PATENT DOCUMENTS

| | | | |
|---|---|---|---|
| 5,782,748 A * | 7/1998 | Palmer | A61B 10/06 600/104 |
| 6,030,402 A | 2/2000 | Thompson et al. | |
| 8,777,232 B2 * | 7/2014 | Yaksich | B23B 31/1253 279/140 |
| 2002/0120289 A1 * | 8/2002 | de Laforcade | A61B 17/1285 606/205 |
| 2004/0064136 A1 | 4/2004 | Papineau et al. | |
| 2007/0179340 A1 | 8/2007 | Jorgensen | |
| 2009/0171159 A1 * | 7/2009 | Jorgensen | A61B 34/71 600/139 |
| 2011/0024997 A1 | 2/2011 | Yaksich | |
| 2012/0083778 A1 * | 4/2012 | McGaffigan | A61B 18/085 606/28 |
| 2013/0253480 A1 * | 9/2013 | Kimball | G06F 19/3481 606/1 |
| 2014/0107690 A1 * | 4/2014 | Ishii | A61B 17/29 606/185 |

FOREIGN PATENT DOCUMENTS

| | | |
|---|---|---|
| WO | 96/03927 A1 | 2/1996 |
| WO | 2012151415 | 11/2012 |
| WO | 2012160715 A | 11/2012 |

* cited by examiner

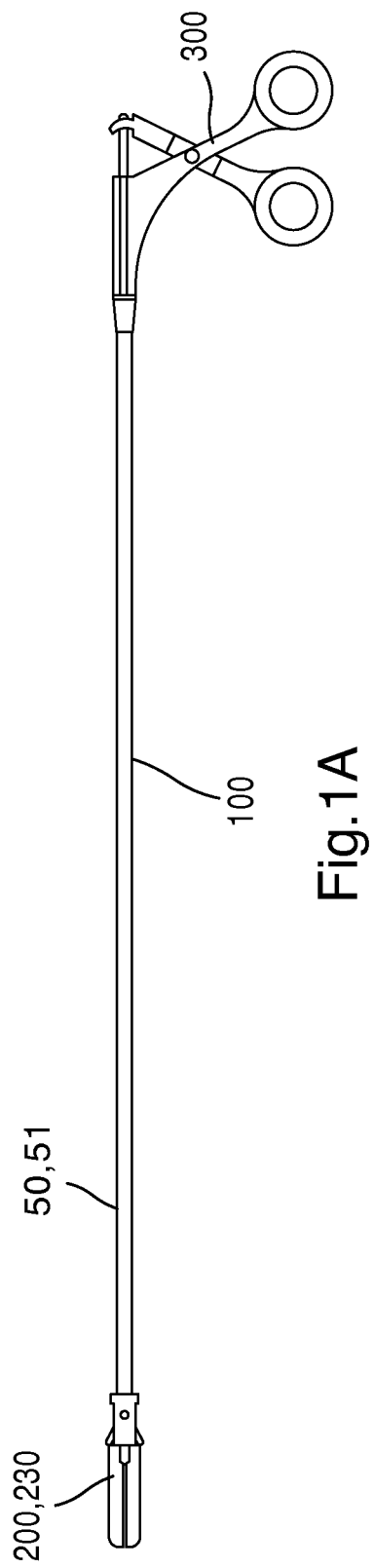
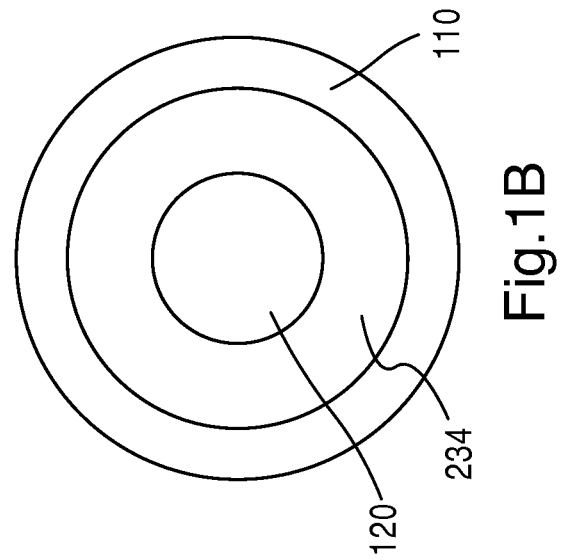
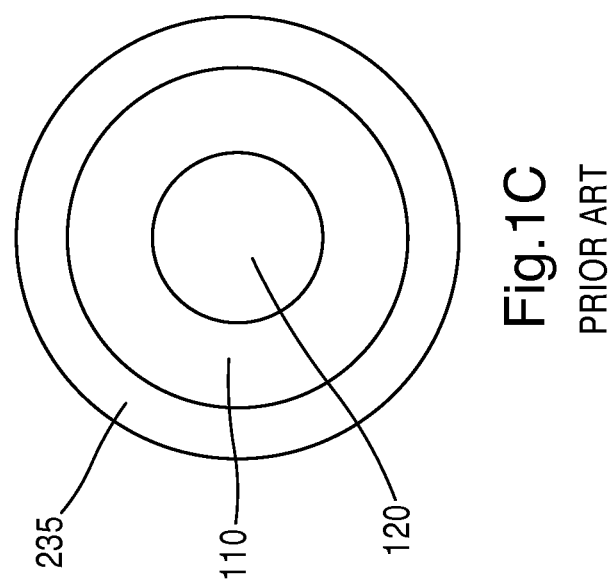
Fig.1A
Fig.1B
Fig.1C
PRIOR ART

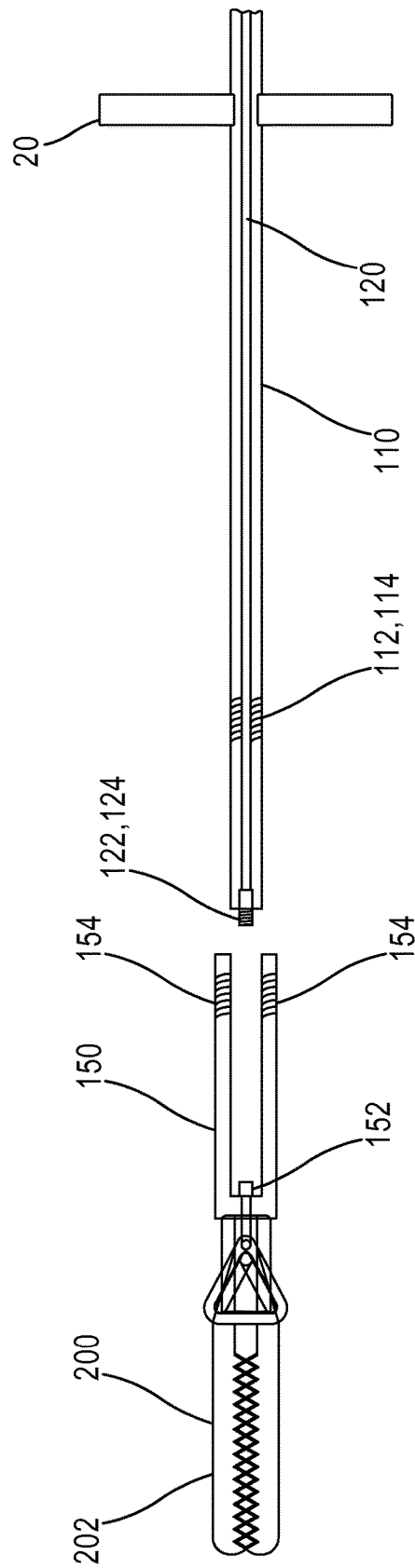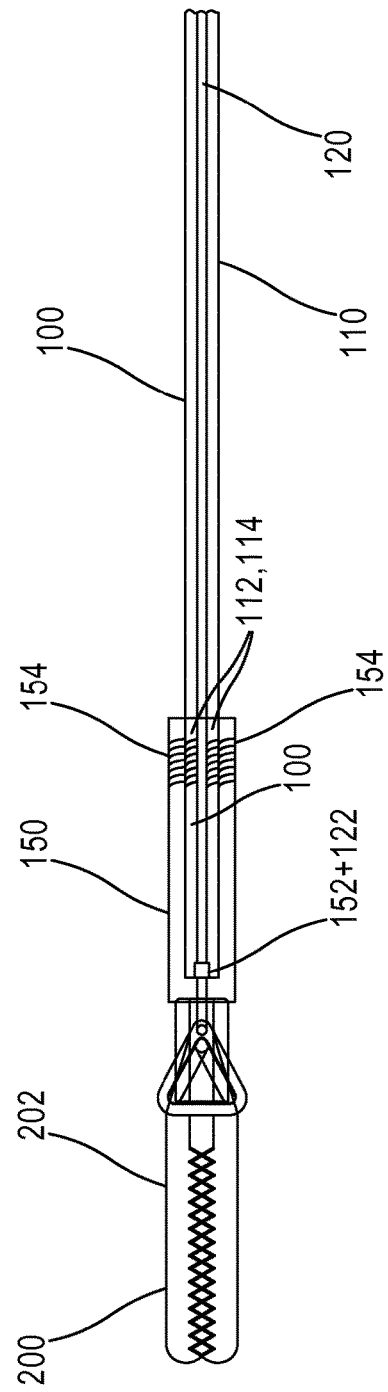
Fig.3A
Fig.3B

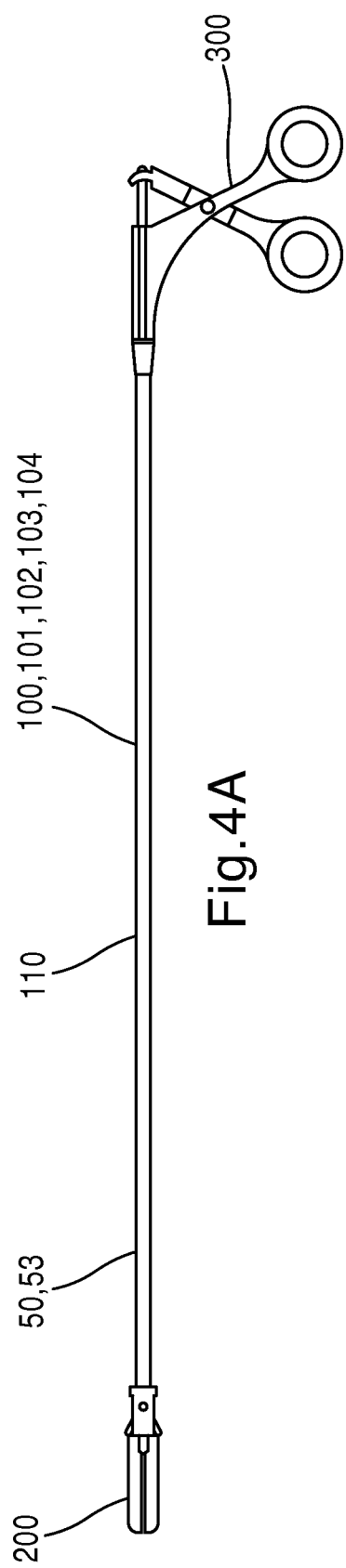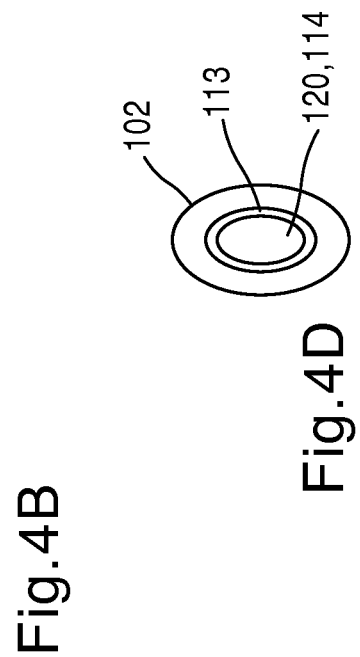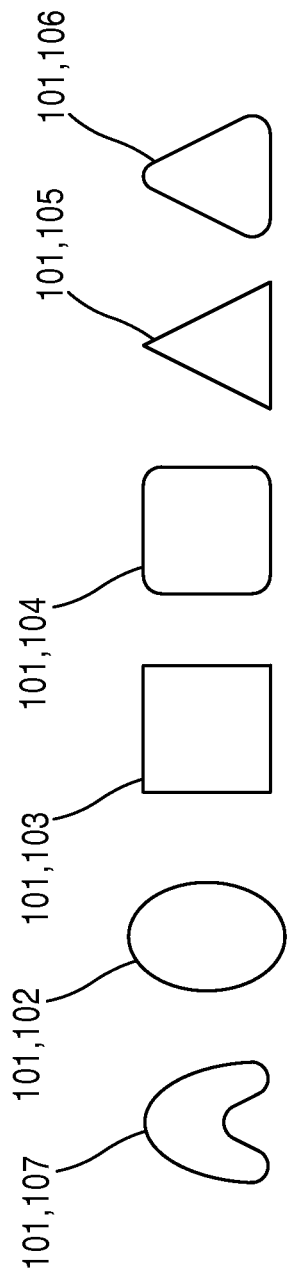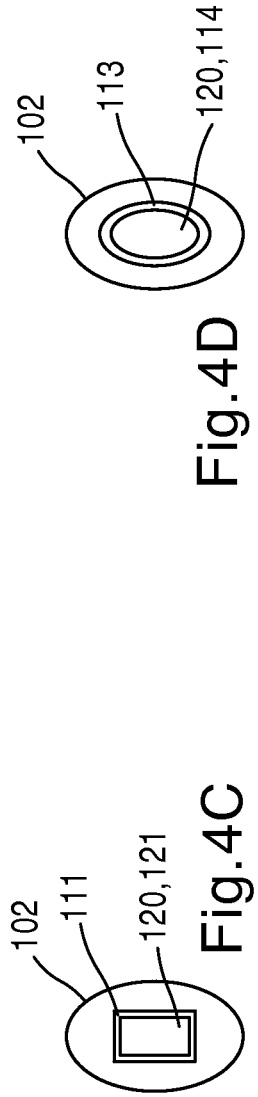

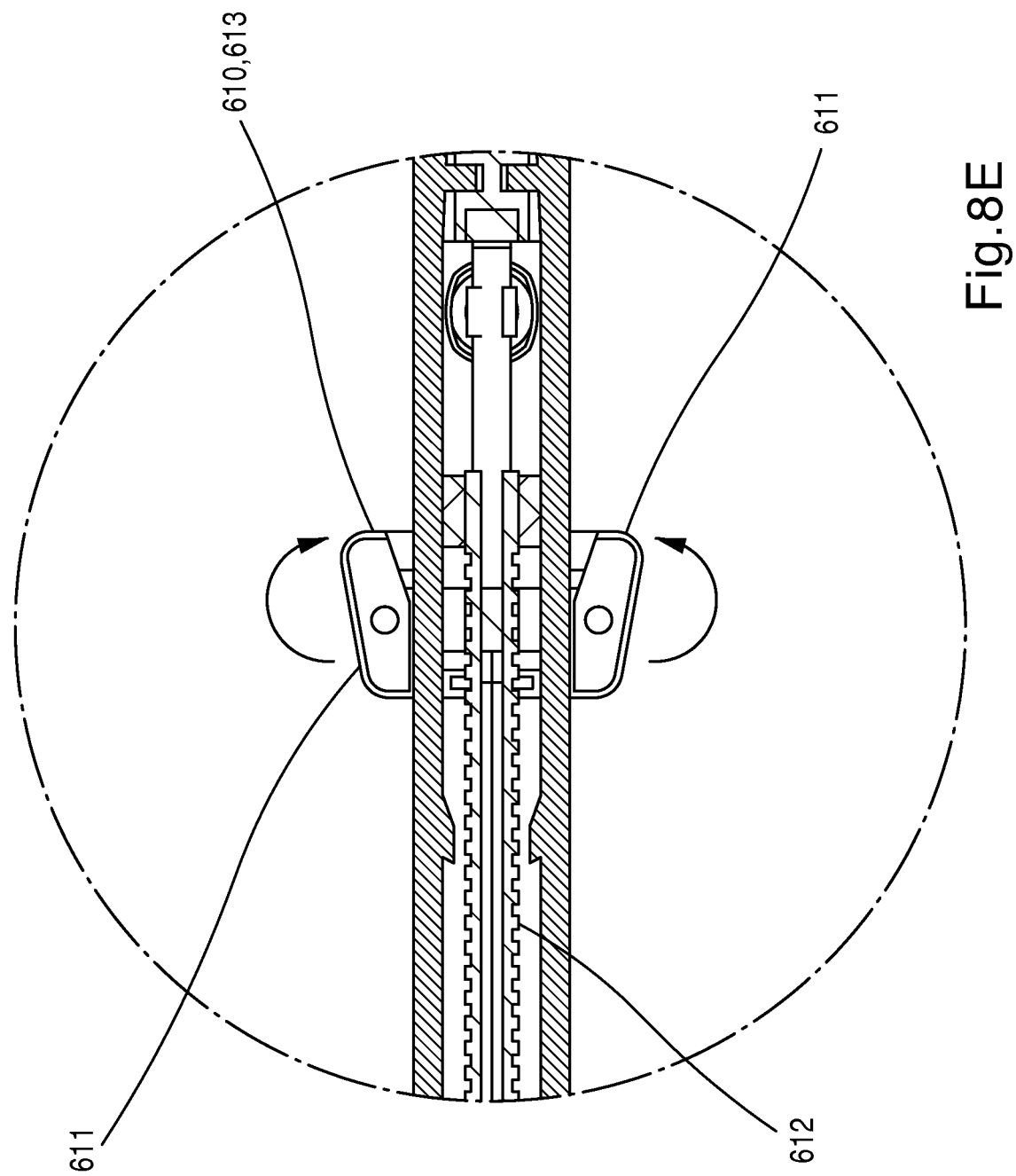

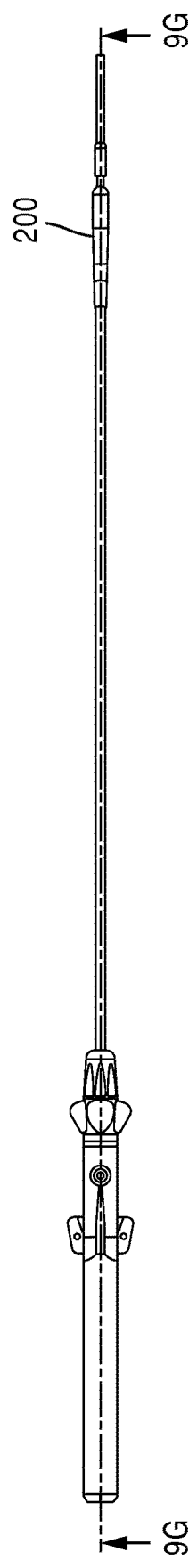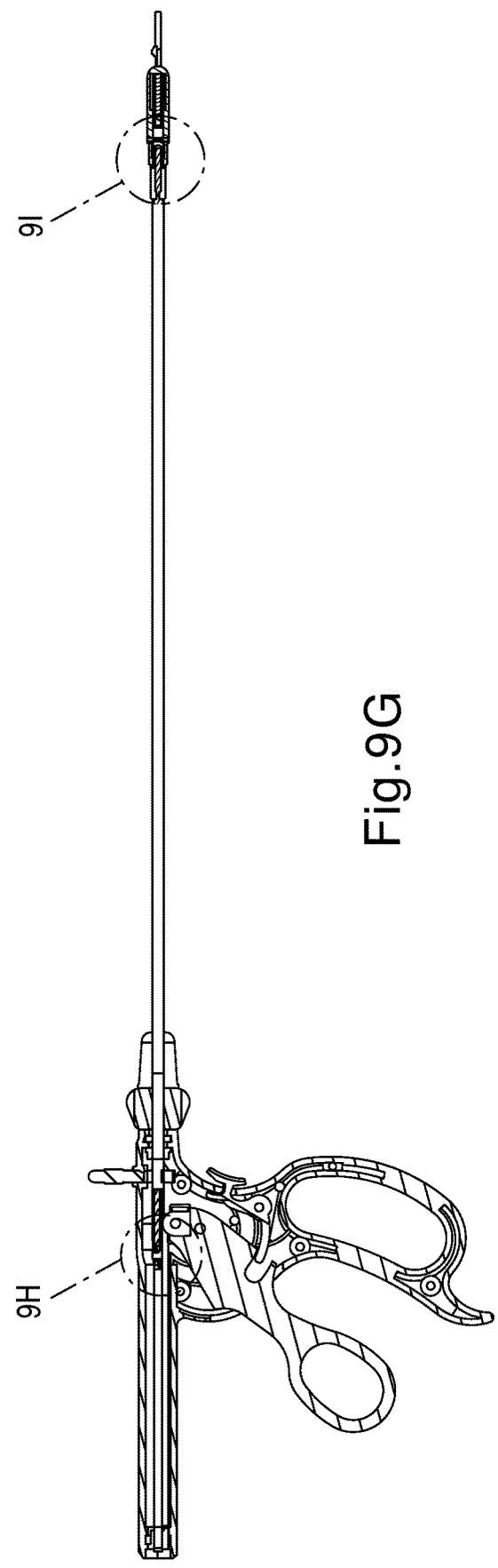
Fig.9F
Fig.9G

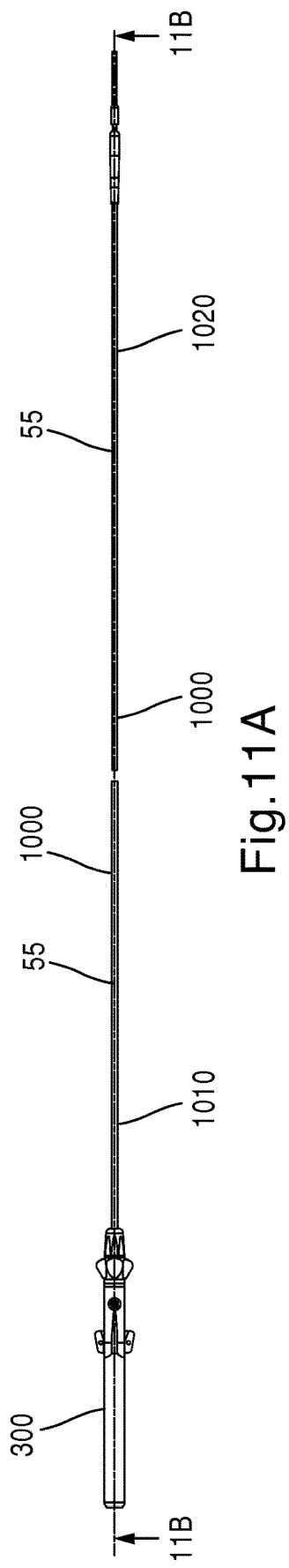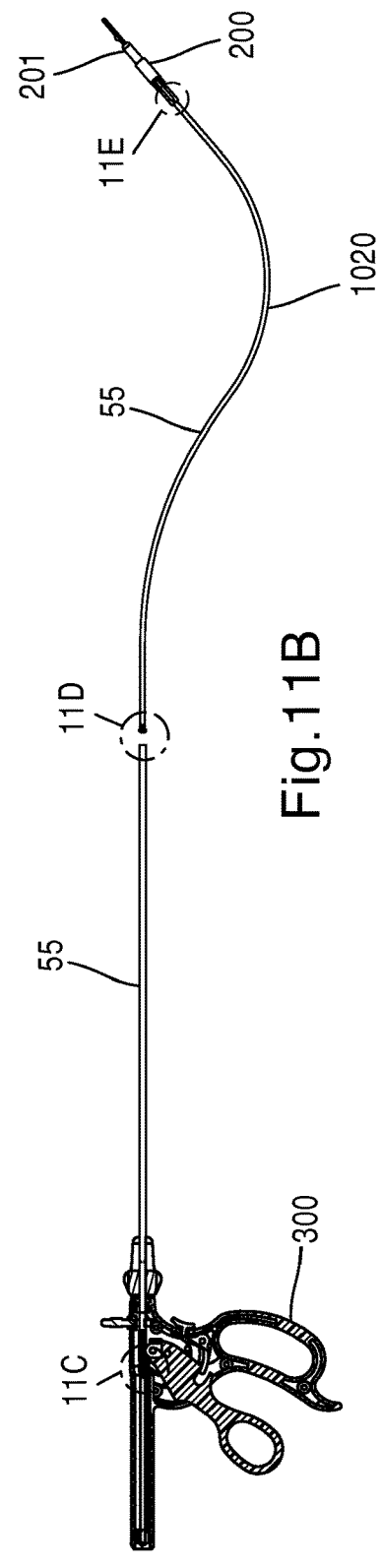
Fig.11A
Fig.11B

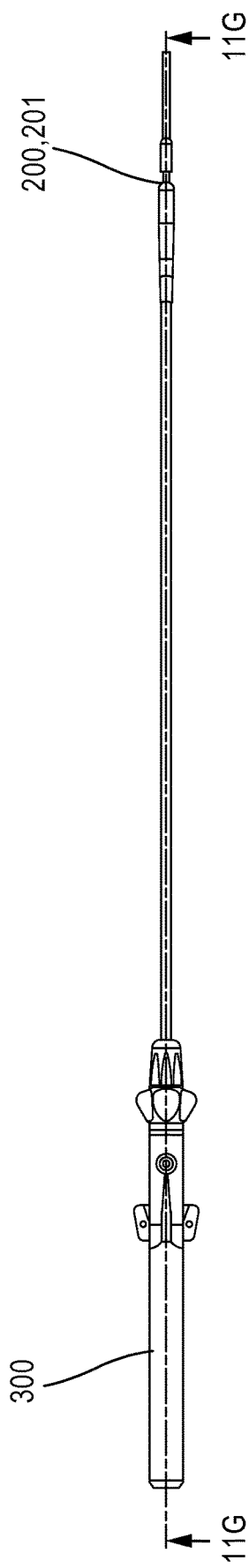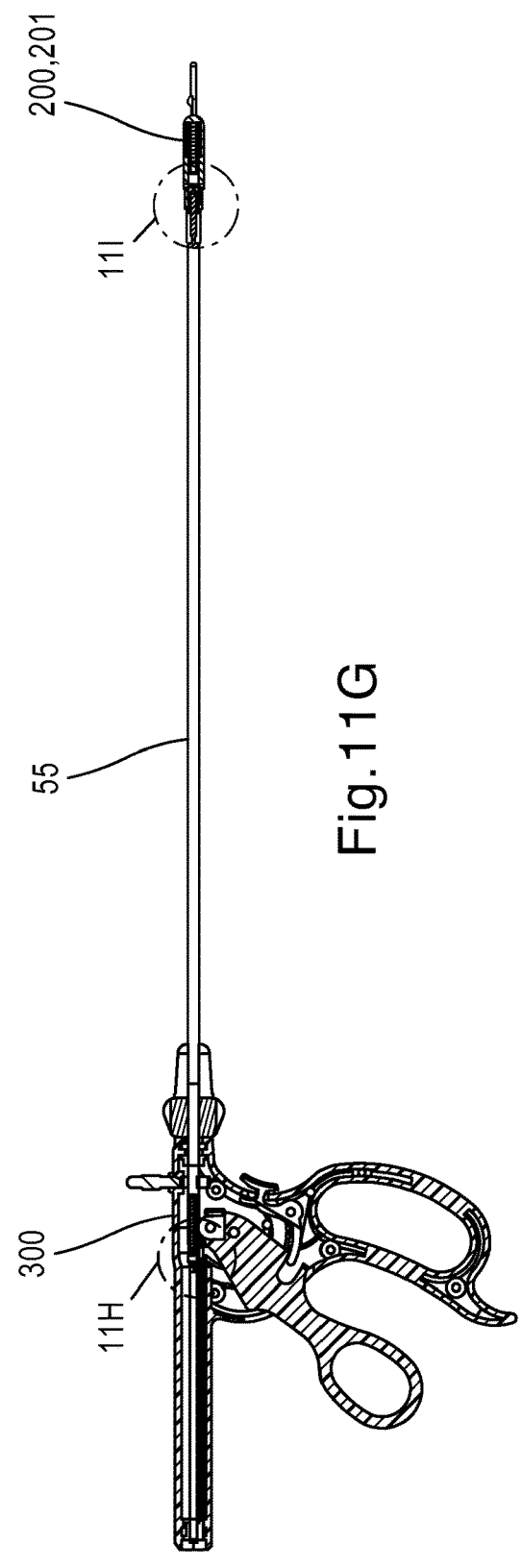
Fig.11F
Fig.11G

RIGID AND FLEXIBLE LAPAROSCOPIC TOOL SHAFTS AND METHODS USING SAME

CROSS-REFERENCE TO RELATED APPLICATIONS

This application claims priority to U.S. Provisional Patent Application No. 61/753,224, entitled, "RIGID AND FLEXIBLE LAPAROSCOPIC TOOL SHAFTS AND METHOD USING SAME," filed Jan. 16, 2013, which is hereby incorporated by reference in its entirety.

FIELD AND BACKGROUND OF THE INVENTION

The present invention, in some embodiments thereof, relates to laparoscopic tools and, more particularly, but not exclusively, enhancements of shafts connecting laparoscopic tool heads to laparoscopic tool handles.

U.S. Patent Application Publication No. 2010/0298774 A1 presents, with reference to its FIG. 23 inter alia, methods by which a distal portion of a shaft of a laparoscopic tool may penetrate (e.g. by puncture) into a body cavity such as the abdominal cavity, traverse a portion of the cavity, exit the cavity through a trocar installed in a wall of the cavity, and while outside the cavity be joined with a laparoscopic tool head. The distal portion of the shaft with its tool head may then be withdrawn through the trocar into the cavity, used there to operate on a tissue, re-extended through the trocar for exchange or removal of the operating tool head, and eventually withdrawn through the entrance wound and removed from the cavity entirely at the end of the operation.

The method there describe presents numerous advantages, one being the avoidance of multiple large wounds to the cavity wall, since in many cases a procedure can be accomplished using a single trocar and a small puncture wound for passage of the tool shaft.

The present application presents embodiments designed to facilitate such procedures.

SUMMARY OF THE INVENTION

The procedure described in the background section can be accomplished using a thin laparoscopic tool shaft, which has the advantage of making only a small entrance wound. It is however a disadvantage of thin shafts that they may in some cases be more flexible than would be desired in a surgical tool. Some embodiments of the invention presented herein comprise devices and methods for enhancing the rigidity of laparoscopic tool shafts, to provide tools rigid enough for safe and efficient laparoscopic operations, yet thin enough to cause (or require) only small entrance wounds in body cavity walls.

In some cases, the procedure described in the background section may be awkward or difficult to accomplish, for example when an entrance wound of a shaft is positioned near the trocar to be used in the procedure. Some embodiments of the present invention presented herein provide tool external tool shafts and/or internal shaft rods which are flexible, thereby facilitating the process of joining a shaft to a laparoscopic tool head using a trocar installed in a body cavity wall to do so.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings:

FIGS. 1A-1F are simplified schematics of laparoscopic tool shaft construction enhancing rigidity by strategic placement of electrically insulating material, according to some embodiments of the present invention;

FIGS. 2A-3B are simplified schematics showing use of rigid sheaths enclosing portions of laparoscopic tool shafts to enhance rigidity of those shafts, according to some embodiments of the present invention;

FIGS. 4A-4E are simplified schematics showing laparoscopic tool shafts shaped to enhance rigidity of the shafts in selected directions, according to some embodiments of the present invention;

FIGS. 11A-11J are simplified schematics showing laparoscopic tools having flexible internal rods, according to some embodiments of the present invention.

DESCRIPTION OF SPECIFIC EMBODIMENTS OF THE INVENTION

Figure 1D:
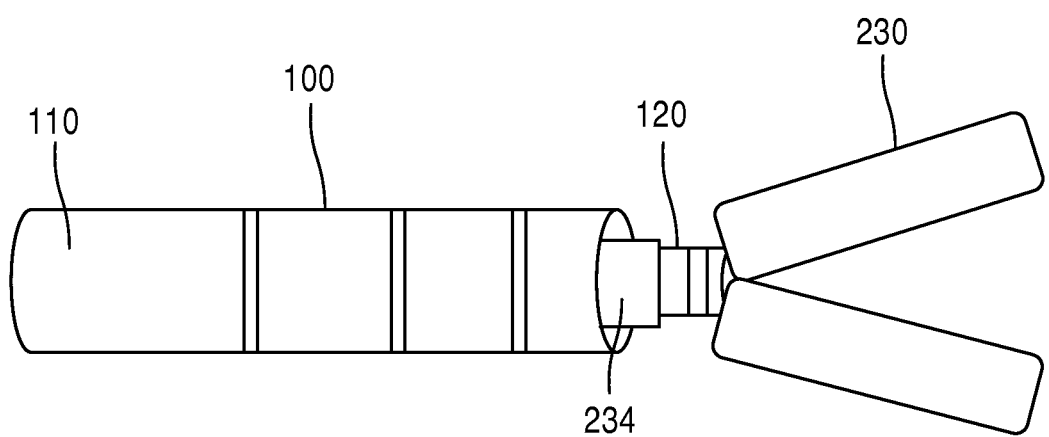
Figure 1D:
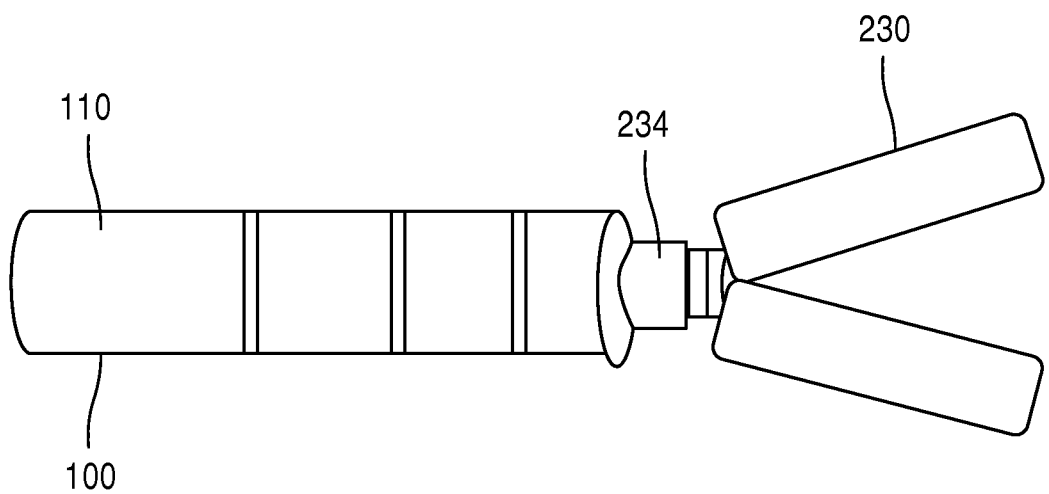

The present invention, in some embodiments thereof, relates to laparoscopic tools and, more particularly, but not exclusively, enhancements of shafts connecting laparoscopic tool heads to laparoscopic tool handles.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

A laparoscopic surgical tool typically comprises a surgical tool head for treating tissue, a handle by which the tool may be grasped or manipulated and controlled by a surgeon, and a shaft connecting head and handle. The term "shaft" (or "shaft 100") is used herein to refer to the portion of the laparoscopic tool which is between the head and the handle. A shaft 100 typically comprises an external portion generally labeled "110" and called an "external shaft portion" or "shaft external portion" or "external portion" or "external shaft" herein. The external shaft is optionally connected (permanently or detachably) to a laparoscopic tool head 200 (also called "operating head 200" and "head 200" herein) and/or to a laparoscopic tool handle 300. External shaft 110 optionally comprises a lumen which may contain an optional internal portion called a "rod 120" herein. Rod 120 is moveable with respect to external shaft 110 and is optionally connected (permanently or detachably) to a laparoscopic tool head 200 and/or to a laparoscopic tool handle 300. Differential movement between rod and external shaft, typically created in a handle 300, is typically used to create and/or control mechanical motion of moveable portions of an operating head 200. Examples of operating heads 200 include grasper, scissor, dissector, hook, needle holder, clip applier, stapler, and camera.

For simplicity, the internal shaft portion is referred to as a "rod" herein, but it is to be understood that the term "rod" is not to be understood to limit the invention to any particular structure of the "rod", for example as the term "rod" is used herein, a "rod" of a laparoscopic tool may optionally be a rod or a cord or a wire or a cable, or any other construction which transmits differential motion as described above. To avoid confusion, a "rod" as defined in this paragraph is also referred to as a "longitudinal connecting element" herein and in the attached claims.

Note that the term "rigidity" as used herein refers to the resistance to bending of a tool shaft or other tool component. So, for example, a shaft which is shortened is thereby made more "rigid" (in the sense of being less bendable) than a longer shaft of the same composition, even though the rigidity of the material and of the cross-sectional structure of the shaft is unchanged.

Rigidity

U.S. Patent Application Publication No. 2010/0298774 A1 disclosed a variety of techniques enabling laparoscopic surgery with a minimum of damage to walls of a body cavity in which the surgery has taken place. One useful result of some of these techniques has been to enable surgery in which a relatively large treatment tool (also called "treatment head" or "head" herein) is controlled and manipulated by a handle outside the body, and the handle is connected to the treatment head by a relatively narrow shaft. Some narrow shafts are between 2 mm and 4 mm in diameter. Narrow shafts are advantageous in that they can pass into a body cavity through a body cavity wall through an opening whose dimensions approximate those of the shaft. Narrow shafts are useful in general, and can be made to pass directly through a body wall or enter the body through various kinds of ports or punctures or small incisions. In general, a narrow shaft requires only a narrow opening, and narrow openings are generally quicker to heal and causes less pain and less disfigurement than the larger holes typically made by classical trocar-based techniques or by insertion of wider tools.

However, it is a disadvantage of narrow shafts that they are more flexible than wide shafts, given the same materials and same structural designs. Flexibility in this context limits the surgeon's control over the treatment head, causes the head shaft to bend when axial or radial or other forces are applied to it, and tends to obscure the surgeons ability to feel the treated tissue through the tool he is holding. In general, with a surgeon's controlling hand on one end of a shaft and a powerful and dangerous surgical tool (e.g. a knife or a coagulator) on the other end of the shaft, one would generally prefer a shaft to be strong and rigid, to allow the surgeon better sensitivity to, and control of, what he is doing.

Accordingly, FIGS. 1A-8F of this application present devices and methods for enhancing rigidity of laparoscopic tool shafts. Some devices and methods here presented may be applied to surgical and other tools of any diameter, size, shaft material, and types of heads and handles, and some may be applied to micro-laparoscopic tools of 2-4 mm width and smaller, and/or to wider tools where radial or axial powers are greater, e.g. to clip appliers, staplers, saws, knives, scissors, etc. In general, at least some embodiments shown in FIGS. 1A-8F and described herein may be applicable to many if not all tools of laparoscopy, micro-laparoscopy, needleoscopy, including laparoscopic and mini-laparoscopic tools (e.g. smaller than 4 mm) which may or may not have detachable heads. At least some embodiments presented herein and which serve to enhance tool shaft rigidity may be applied to tools subject to disassembly (as shown in some of the figures) and/or to tools not subject to disassembly.

Embodiments enhancing tool shaft rigidity and presented herein below include at least the following categories, optionally usable separately and/or in concert:

Devices and methods enhancing overall rigidity of a shaft designed to carry electric current by positioning electrical insulation required in a tool shaft at a position and in a configuration different from that known in the art, particularly in art relating to diathermia and monopolar electrical applications.

Devices and methods enhancing rigidity by providing a reinforcing sheath over a portion of a shaft to enhance rigidity of that portion, thereby enhancing overall rigidity of the shaft.

Some sheaths are presented for use in a body cavity between body cavity wall and treatment head and as optionally connectable to treatment head and/or manufactured as an extension of a tool head.

Some sheaths are presented for use outside a body between body wall and tool handle, and are optionally connectable to, or manufactured as an extension of, a handle.

Devices and methods for enhancing overall rigidity of a shaft by shortening rod and shaft, using:

medial shaft connections and optionally addable and/or removable shaft/rod extensions, and/or Tool handles able to be variably positioned with respect to an extra-body portion of a shaft, and thereby optionally able to enhance rigidity of a tool shaft by shortening the distance between tool handle and tool head.

Devices and methods enhancing rigidity of a shaft in selected directions by providing non-cylindrical shafts and/or shaft components.

Enhancing Shaft Rigidity of a Laparoscopic Tool which Comprises Electrical Insulation FIGS. 1A and 1B present a laparoscopic tool 50 also labeled 51 which comprises a tool head 200 which is an electrical tool head 230. Tool 51 achieves enhanced rigidity by positioning electrical insulation required in the tool in at a position other than surrounding the tool shaft, where it is generally positioned in configurations known in the art.

Tool head 230 may be, for example, a diathermy head, a coagulator, and/or any other head 230 equipped to use electricity. Shaft 100 of tool 50 comprises an outer shaft 110 and a rod 120, rod 120 being within a lumen of outer shaft 110. As shown in FIG. 2B which is a cross section of shaft 100 of tool 51, electrical insulation 234 in tool 51 isolates rod 120 which carries current to head 230. In some embodiments insulation 234, which isolates current-carrying rod 120 from electrical contact with patient tissues, is positioned within external shaft portion 110 and outside of internal rod 120. External shaft portion 110 is optionally metallic but is unconnected to the electricity source. Optionally insulation 234 is provided as an interior layer of external shaft portion 110. Alternatively, optionally insulation 234 is provided as an exterior layer to rod 120. Optionally, insulation 234 may be an independent insulating layer positioned between but not connected to rod 120 and outer shaft 110. Optionally, rod 120 may comprise a plurality of longitudinal components isolated from one another, to carry bipolar electric current.

FIG. 1C shows a conventional structure known to prior art, in which an isolation layer 235 is provided on the exterior of an external shaft portion 110 of a shaft 100. It is an advantage of tool 51 that for a same shaft diameter, a proportionally larger amount of external shaft portion material is present in tool 51. Since external shaft 110 may be made of metal or other very hard material whereas insulating material may be less hard, shaft 100 of tool 51 may have an advantage of stiffness as compared to the configuration shown at FIG. 1C.

Insulation 234 between rod 120 and external shaft 110 may optionally extend to a shaft-rod covering 2341 as shown in FIG. 1D. In some embodiments external insulation on or near an operating head and/or on a distal extremity of a shaft may be used in combination with internal insulation used in the main body of the shaft.

Figure 1E:
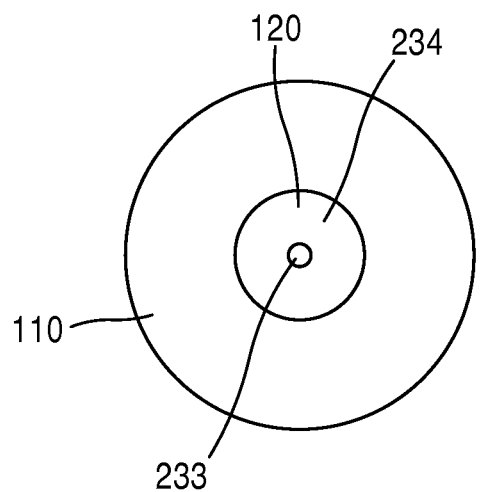
Figure 1F:
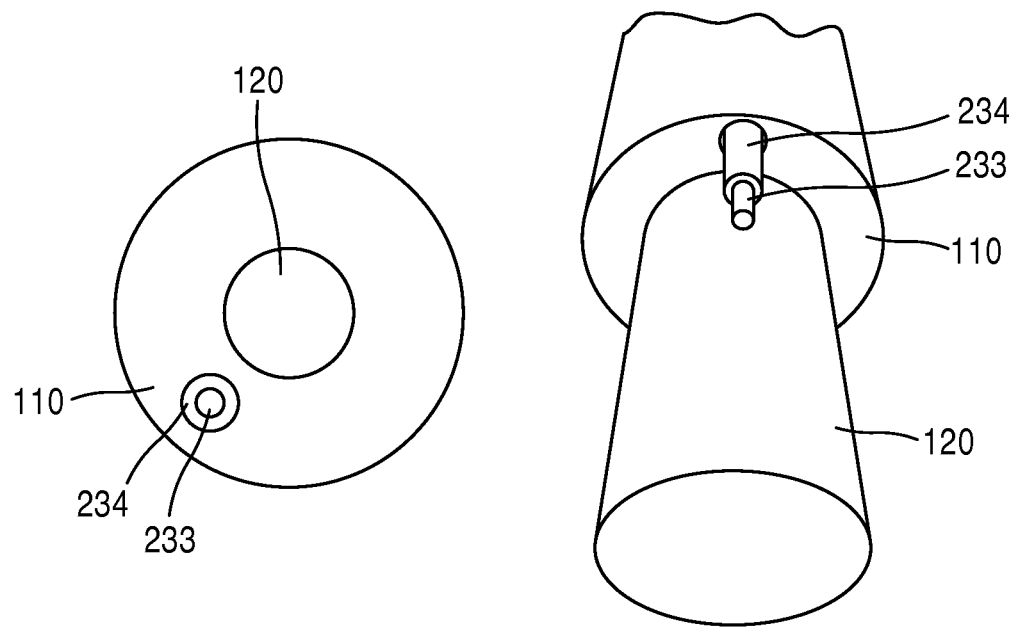

Further alternative embodiments, also enhancing shaft rigidity by isolating a current-carrying element, optionally an electrical wire, without providing electrical isolation on the exterior of external shaft portion 110 are shown in FIGS. 1E and 1F. FIG. 1E shows a shaft which comprises a rod 120 composed of an electrically insulating material (e.g. plastic, ceramic) which serves both the mechanical functions of rod 120 and the electrical isolating function of insulation 234, isolating an electric wire 233 which passes the length of the shaft and is isolated from contact with external shaft 110, which therefore needs no external insulation of its own. FIG. 1F shows (in both a cross-sectional view and a perspective view) an embodiment in which an electrical conductor 233 passes through a small lumen in an external shaft portion 110. Optionally, external shaft portion 110 is made of electrically insulating material. Optionally, conductor 233 is enclosed in an electrical insulating material 234 as shown in the Figure.

Enhancing Rigidity by Providing a Reinforcing Sheath Over a Portion of a Shaft:

Attention is now drawn to FIGS. 2 and 3, according to an embodiment of the present invention, in which rigidity of a laparoscopic shaft 100 is enhanced by a reinforcing sheath 150 over a portion of shaft 100.

Figure 2A:
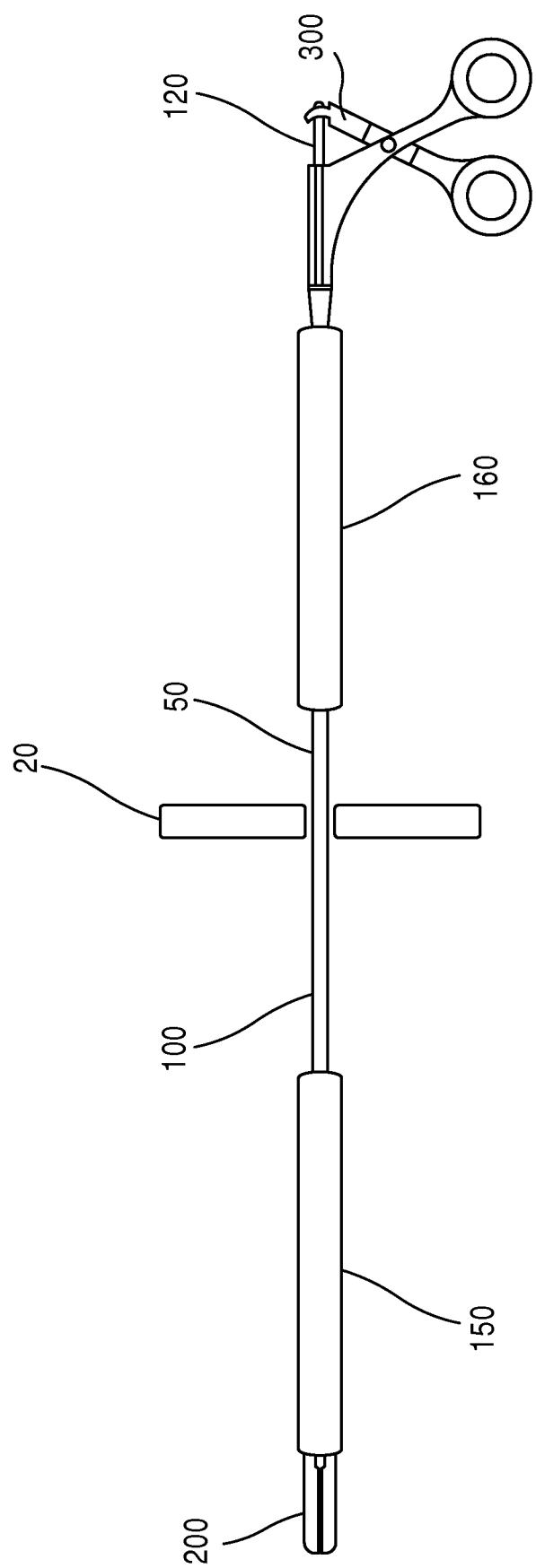
Figure 2B:
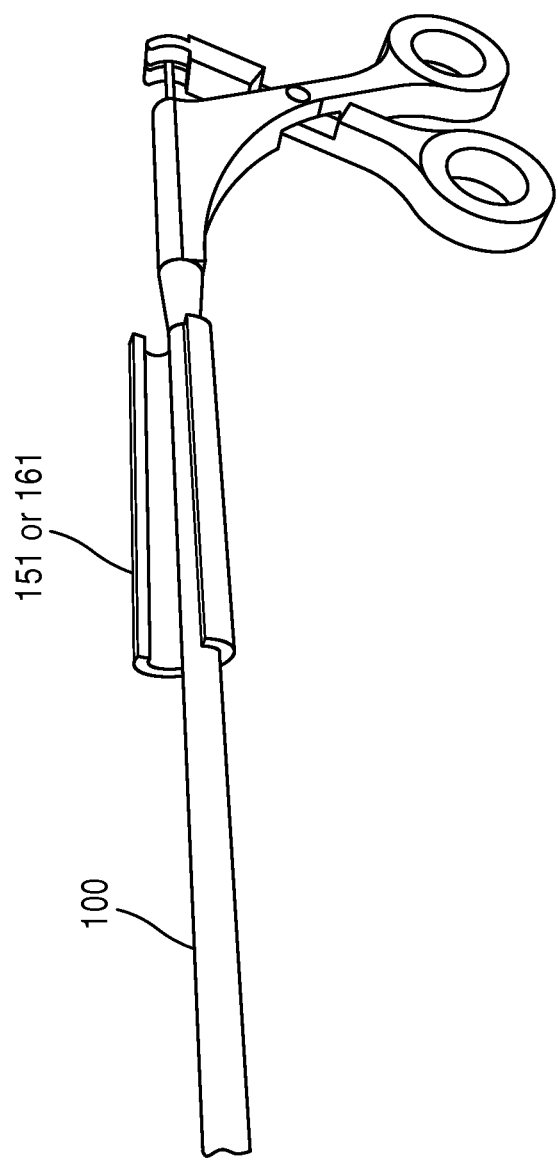

FIG. 2A presents a laparoscopic tool 50 having a distal portion penetrating through a body cavity wall 20 such as an abdominal wall. Tool 50 may also be thought of [?] as penetrating through any body tissue or natural orifice or created orifice directly, optionally through a body tissue or through a port. Tool 50 is equipped with a treatment head 200 at its distal end. A rigidity-enhancing sheath 150 is shown enclosing a portion of shaft 100 to add rigidity to that portion of shaft 100 which is within the body cavity. FIG. 2 also presents a sheath 160 also enclosing a portion of shaft 100 and external to the body cavity. Lengths of shafts 150 and 160 as shown in the figure are exemplary only, and not to be considered limiting, and shafts of a variety of lengths, as appropriate for various clinical conditions, are contemplated.

Optionally, sheath 160 may be slid over a proximal portion of shaft 100 prior to connecting shaft 100 to handle 300. Optionally, sheath 160 may be slid over a distal portion of shaft 100 prior to insertion of a distal portion of shaft 100 into a body, and slid from there onto a proximal portion of shaft 100.

Figure 2C:
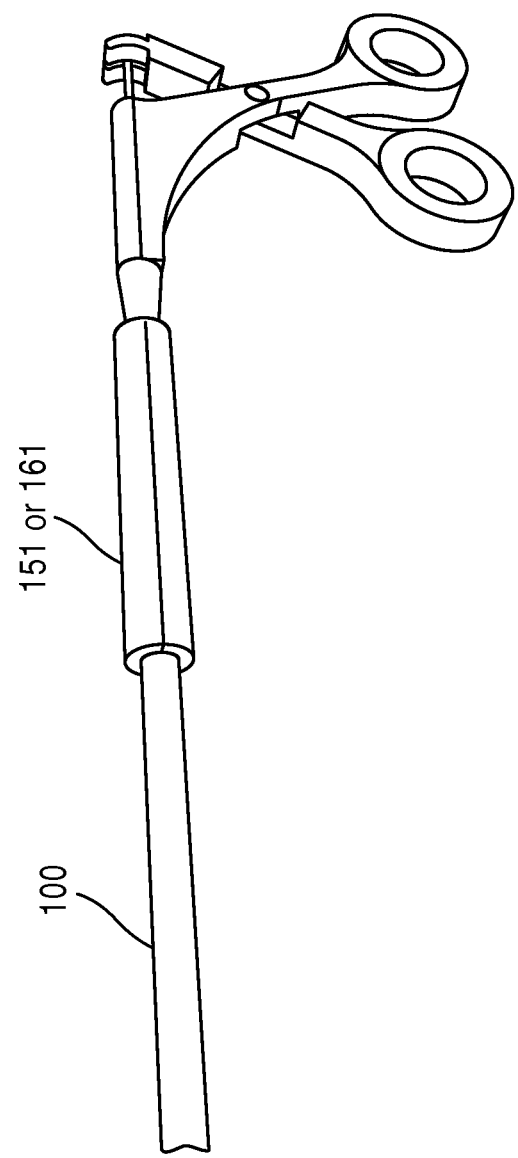

Optionally, sheath 160 may be manufactured in one or more parts which may be clipped onto or attached to or around shaft 100, for example as two hinged parts which snap together around shaft 100, as shown in FIGS. 2B and 2C, where a clippable version 161 of a shaft 160 (and/or a clippable version 151 of a shaft 150) is shown in open configuration in FIG. 2B and in closed configuration in FIG. 2C. Optionally, clippable versions 161 and 151 may comprise handles to facilitate assembling and disassembling them.

Optionally sheath 150 may be slid over a distal portion of shaft 100 prior to connecting shaft 100 to head 200. Optionally, sheath 160 may similarly be clipped onto or around a distal portion of shaft 100. Optionally, sheaths 150 and/or 160 may be of variable widths or lengths or can have adjustable lengths. For example, a sheath 150 and/or 160 may have a telescoping configuration and/or comprise first and second parts having screw threads enabling the first and second parts to advance one within another to a controllable degree therefore enabling a user to control length of the sheath. Sheaths 150 and 160 serve to prevent or reduce bending of shaft 100 when lateral pressure or any other force is applied to shaft 100, e.g. by a surgeon applying force to a handle 300.

Extra-body rigidity sheath 160 and intra-body rigidity sheath 150 can be used in concert, or one or the other may be used alone.

Sheath 160 is optionally connectable to handle 300 and also may optionally be manufactured with and/or be permanently connected to handle 300, as an extension thereof.

Sheath 150 is optionally connectable to head 200, and optionally may be manufactured together with and/or permanently connected to head 200 as an extension thereof. This option is shown in further detail in FIG. 3.

In FIG. 3 shows a tool head 202 which comprises and/or connects to a sheath 150. Head 202 comprises a rod-connecting element 152 which is optionally a screw connection, e.g. a male or female connector comprising screw threads. Sheath 150, embodied as an extension to head 202, comprises a shaft-connecting element 154, optionally screw threads on a portion of sheath 150. Rod 120 comprises a connector 122, optionally comprising screw threads 124, on or near its distal end. External shaft 110 also comprises a connector 112, optionally comprising screw threats 114, optionally displaced slightly from its distal end as shown in the figure.

FIG. 3A shows shaft 100, including external shaft 110 and internal rod 120, disconnected from head 202 and sheath 150.

FIG. 3B shows shaft 100 connected to head 202 and sheath 150, with rod-connecting element 152 engaging rod connector 122 and shaft-connecting element 154 engaging shaft connector 112. As may be seen in the figure, sheath 150 extends over a distal portion of shaft 100, reducing its ability to bend and enhancing rigidity.

Enhancing Rigidity of a Shaft of a Laparoscopic Tool in Selected Directions

Attention is now drawn to FIGS. 4A and 4B, which present methods and devices for enhancing rigidity of a shaft of a laparoscopic tool in selected directions by providing non-cylindrical shafts and/or shaft components. In some embodiments heads may be connected to shafts in a particular orientation so that pressures applied to the heads with have a desired orientation with respect to the shafts.

It is a general goal of laparoscopic surgery to minimize the size of wounds to the wall of a body cavity when practicing laparoscopic surgery to body tissues within that body cavity. Applicant has noted, however, that the body tissues surrounding an incision or puncture opening in a body cavity wall are flexible, and will adapt readily if, after making an opening (e.g. a puncture) in an abdominal wall, an oval shaped trocar, or a laparoscopic shaft without trocar or encased in a flexible trocar, is inserted in the opening. Generalizing, applicant has observed that it is possible to provide laparoscopic shafts of oval, square (optionally with rounded corners), triangular (optionally with rounded corners) and/or other non-circular cross-sections, into circular or arbitrarily shaped openings in a body cavity wall, and that the body tissues, being somewhat elastic, will adapt themselves around the inserted shape. Consequently a surgeon may make a simple puncture wound or incision in a body wall and introduce therein a laparoscopic tool shaft in a shape of his choosing.

In some surgical procedures, for example in sawing and/or cutting or holding or lifting tissue, it may be desirable for a surgeon to be able to apply strong pressure in a particular direction. Embodiments shown in FIGS. 4A-4D facilitate this process by providing, for a given cross-sectional area of a laparoscopic (or other) tool shaft, shaft designs which enhance rigidity of the shaft in selected directions. These would optionally be used with tool heads mounted in orientations which enable a surgeon to apply pressure in desired directions with respect to the specific type of head mounted on the shaft, without necessarily increasing the over-all cross-sectional area of the shaft. This is desirable since an increase in cross-sectional area of a shaft requires an increase in the size of the penetration wound in a body wall needed to accommodate the shaft, leading to additional pain, longer recovery times, and possibly additional scarring.

FIG. 4A shows a laparoscopic (or other) tool 50, also labeled 53 which comprises a shaft having a non-cylindrical external form 101 along at least 20% of its length, or along at least 30% of its length, and optionally along its full length. FIG. 4B shows various examples of optional external forms for shaft 100, including oval (102), square (103), square with rounded corners (104), triangular (105), and triangular with rounded corners (106). Other non-cylindrical forms are also contemplated as embodiments of the present invention, including non-regular forms 107.

Figure 4E:
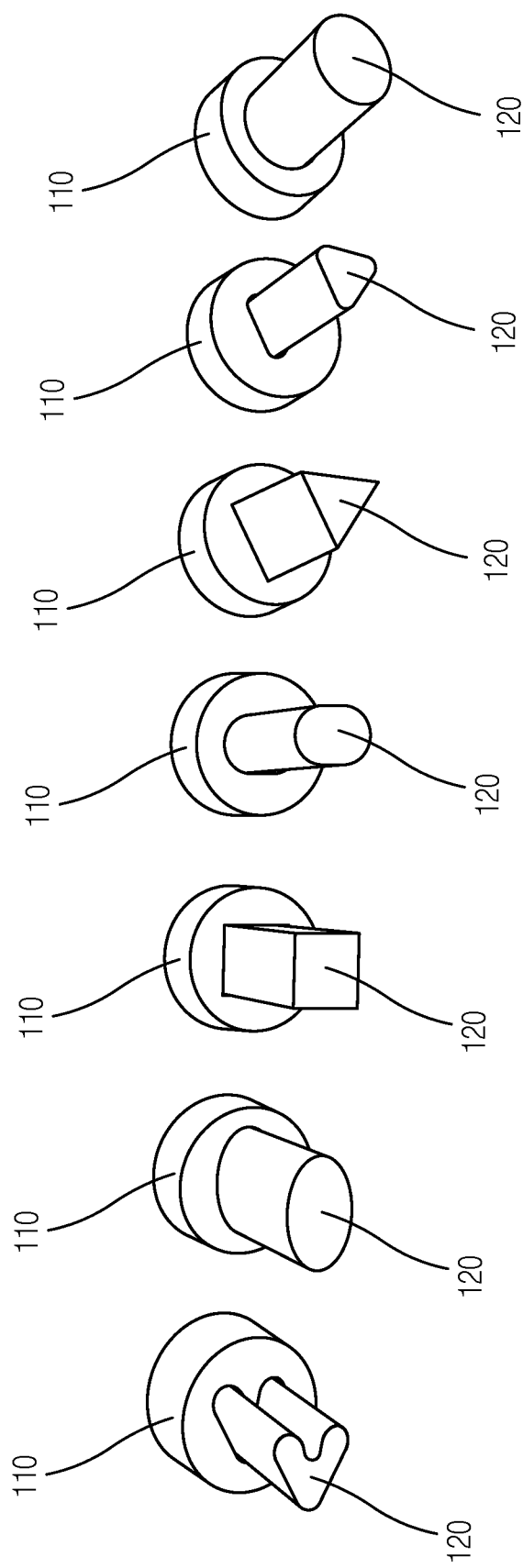

FIG. 4C is provided to show that internal components of shaft 101 may have cross-sectional forms which differ from the external form of external sheath portions 110 thereof. In the exemplary embodiment shown in the figure, a shaft 100 having an external shaft portion 110 with oval shape 102 may comprise, for example, a rectangular lumen 111 and a rectangular rod 121 therein. Other shape combinations are possible. FIG. 4D is provided to show that internal components of shaft 101 may have cross-sectional forms which are congruent or partially congruent to the outer shapes of external shaft 110. In an exemplary embodiment shown in the figure, an oval external shaft 102 comprises an oval lumen 113 containing an oval rod 114. FIG. 4E shows a variety of shaft forms in which oval and/or circular external shaft cross-sections are combined with internal rods of a variety of forms not necessarily congruent with the external shaft cross-sections.

Enhancing Rigidity of a Shaft by Shortening the Shaft: Multiple Connectable Shaft Parts Attention is now drawn to FIGS. 5A-5C, which are simplified schematics of a laparoscopic tool shaft 105 which comprises at least two separable longitudinal shaft segments 107 and 109 and a medial connection mechanism 119 for connecting and disconnecting the separable shaft segments.

Figure 5A:
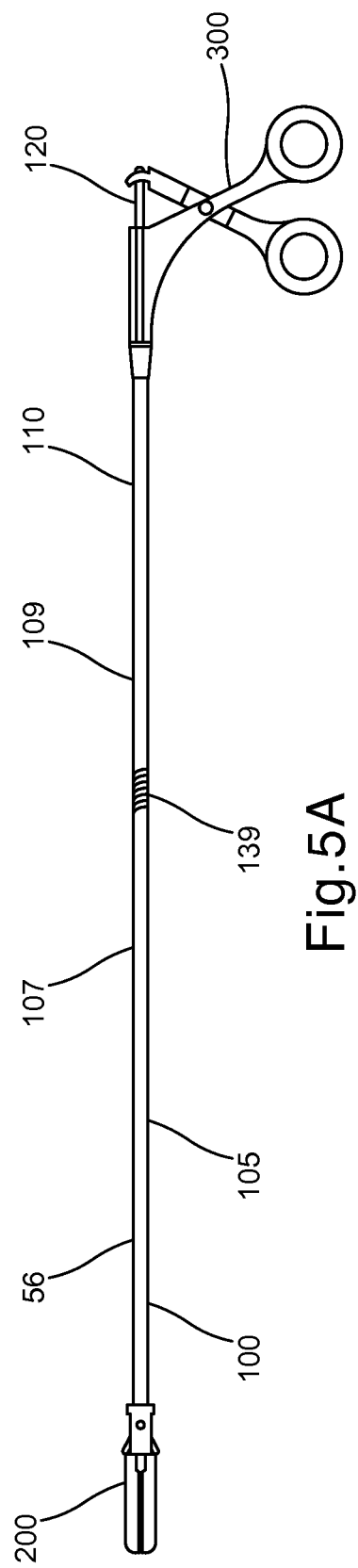
FIGS. 5A-6B are simplified schematics showing use of laparoscopic tool shafts which comprise a plurality of detachable segments to enhance rigidity of a laparoscopic tool shaft by shortening the shaft in some circumstances, according to some embodiments of the present invention.

FIG. 5A shows a tool 56 which comprises a shaft 100, here labeled 105 because it comprises separable and connectable sections 107 and 109, and a medial connection mechanism 139 by which they can be attached to each other to form a relatively long shaft, or detached one from another to form a relatively short shaft comprising only one of parts 107 and 109, but not both. Tool 105 is useful because in some circumstances, including the use of methods taught in U.S. Patent Application 2010/0298774 A1 it is convenient or necessary to have a long shaft during some tool manipulations (e.g. for extending the shaft from a puncture into a body cavity and out through a trocar, and there connecting or removing a treatment head), yet as explained above, during some surgical manipulations a shorter and therefore stiffer shaft is preferable. Tool 105 may be used with two or more separable shaft portions connected during some phases of use, and one or more shaft portions (e.g. part 107) may be removed during other phases of tool 105 use.

Figure 5B:
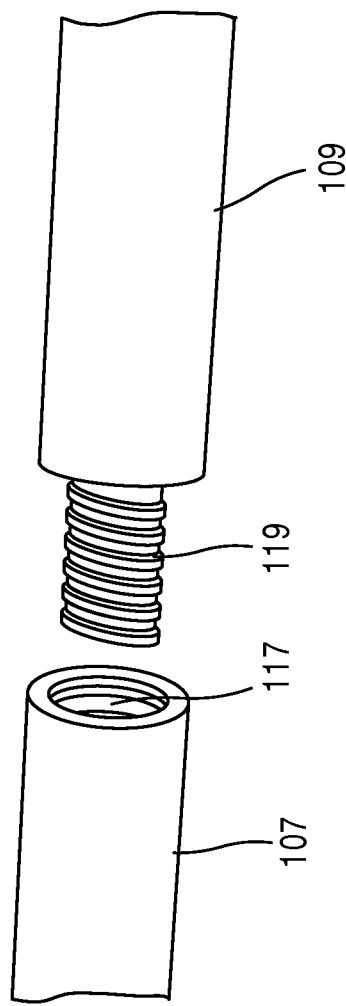

FIG. 5B shows views of the external shaft portions of shaft parts 107 and 109, showing connection mechanisms 119 and 117, which in this exemplary embodiment are male and female screw threads. For simplicity of the figure, rod 120 is not shown in FIG. 5B.

Figure 5C:
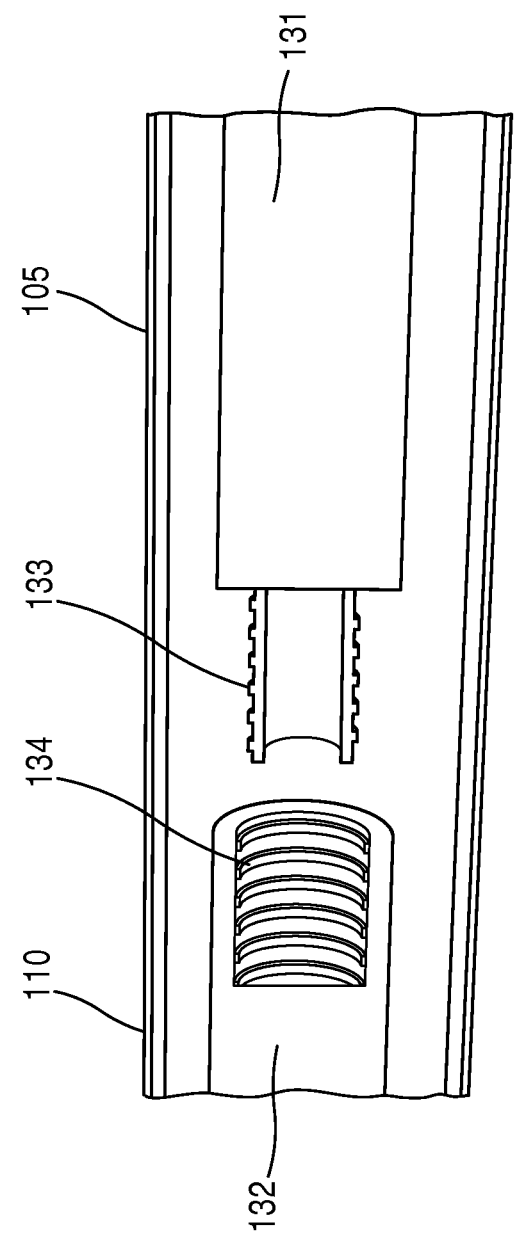

FIG. 5C shows a portion of shaft 105 showing an uninterrupted portion of external shaft portion 110 of shaft 105, enclosing two joinable sections of a rod 120, labeled 132 and 131. A connection mechanism 133 and 134, also screw threads in this exemplary embodiment, are useable to connect and disconnect sections 132 and 131 to lengthen or shorten rod 120 of shaft 105. Rod and shaft connections may optionally be positioned at same longitudinal positions of a shaft, or optionally may be longitudinally displaced one from another. Optionally, click connections, bayonet connections, and other connecting mechanisms may be used.

In some embodiments, connection mechanisms 133, 134, 117, and 119 together comprise medial connection mechanism 139, which serves to connect and disconnect an external shaft portion of a first segment with the external shaft portion of a second segment, and which serves to connect and disconnect a rod portion (e.g. 132) of the first segment to a rod portion (e.g. 131) of a second segment.

In some embodiments, threads of connectors 133 and 119 are so oriented that turning part 107 with respect to part 109 can connect both rod and external shaft. In some embodiments the threads are oppositely oriented, so that shaft and rod must be turned in opposite direction to connect (or disconnect) them. This latter arrangement may serve to prevent accidental uncoupling during an operation.

Figure 6A:
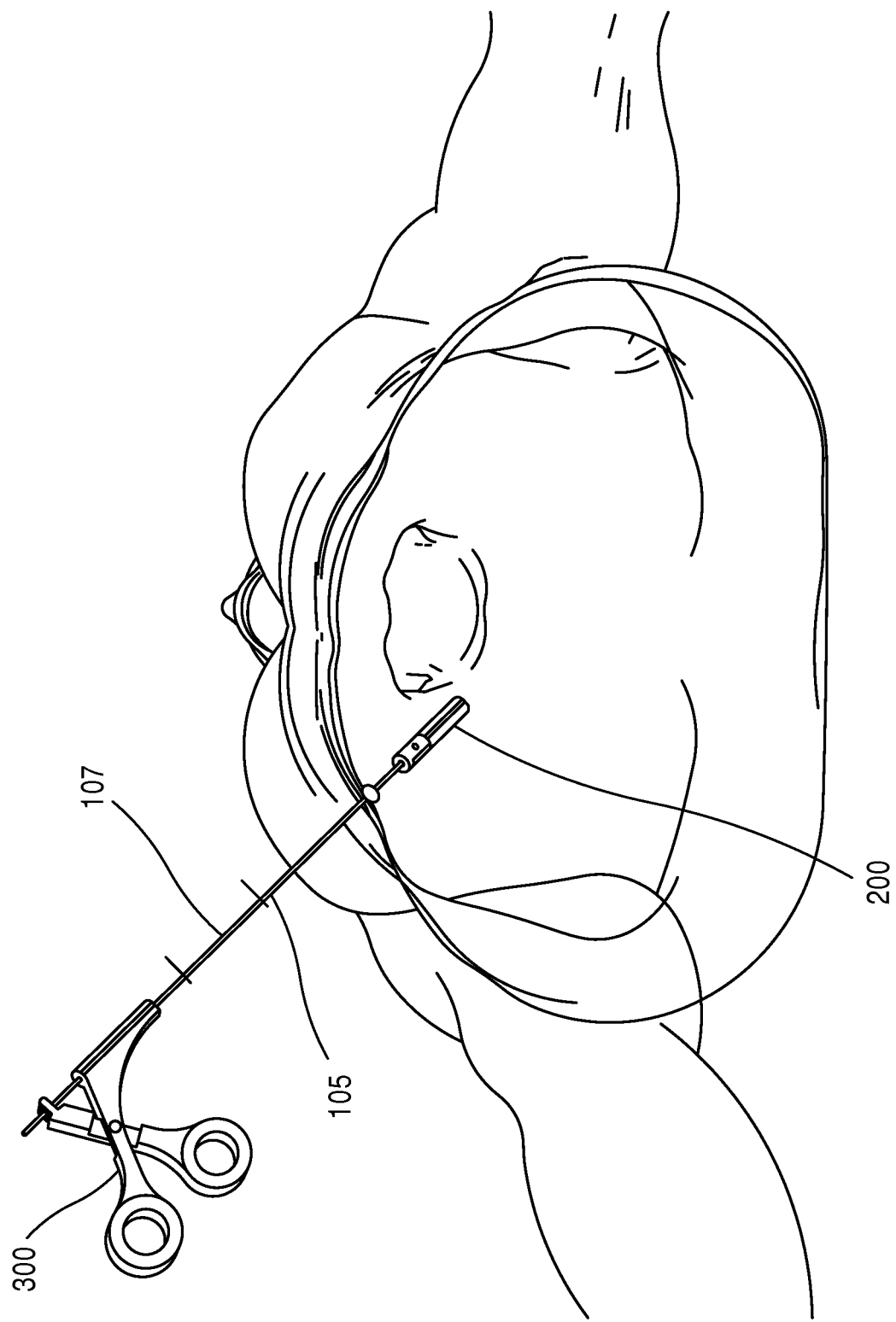
Figure 6B:
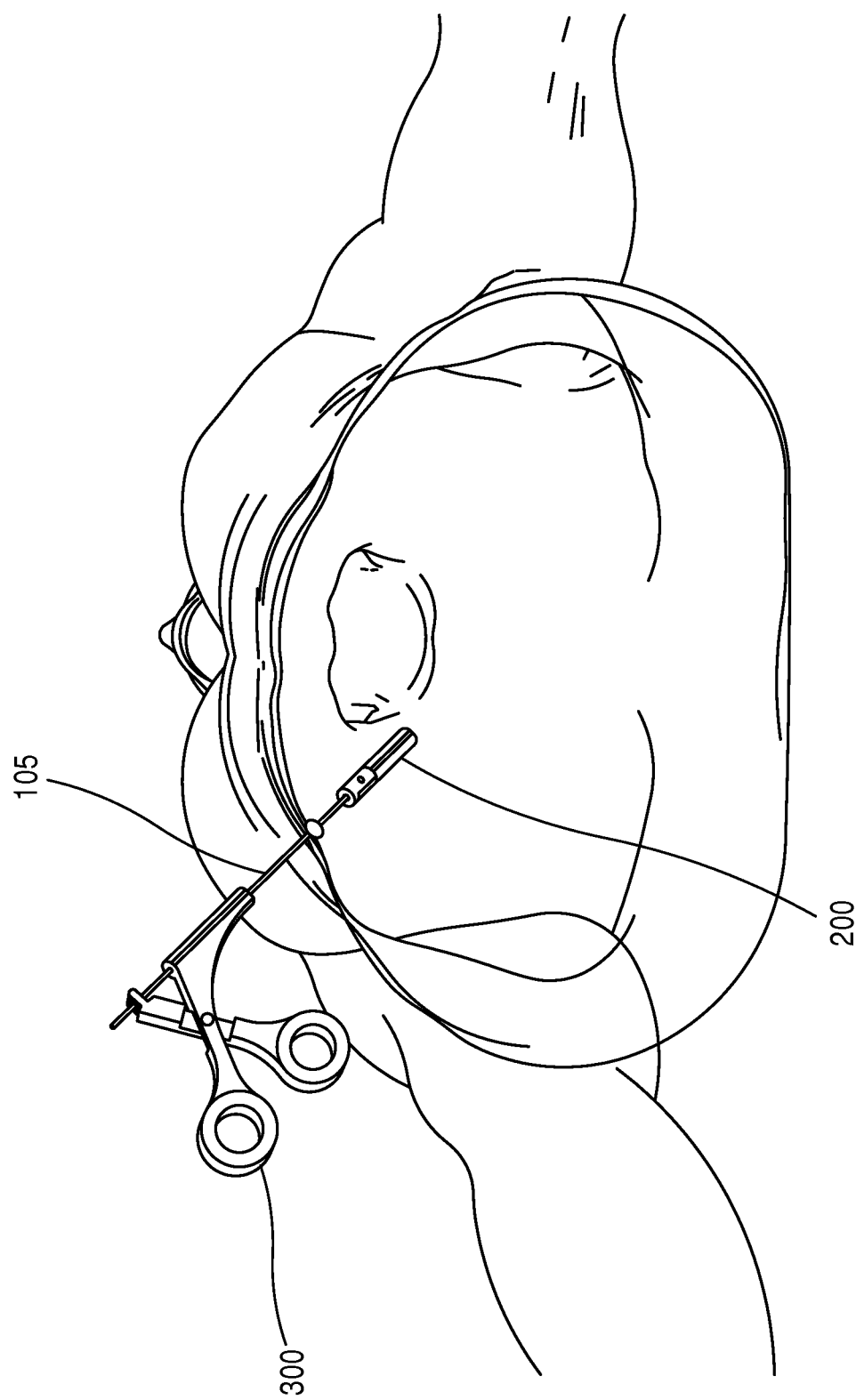

Attention is now drawn to FIGS. 6A and 6B, which show methods of use of a laparoscopic tool which comprises a shaft 105 with severable connectable portions. FIG. 6A shows shaft 105 in a long configuration, comprising several detachable shaft portions, including a portion 107. FIG. 6B shows the same tool after removal for portion 107. As may be seen in the figure, shaft 105 has been shortened and thereby made more rigid. Optionally, removable shaft portions may be added and/or removed at a proximal part of a shaft and/or a medial part of a shaft and/or a distal part of a shaft.

Figure 7A:
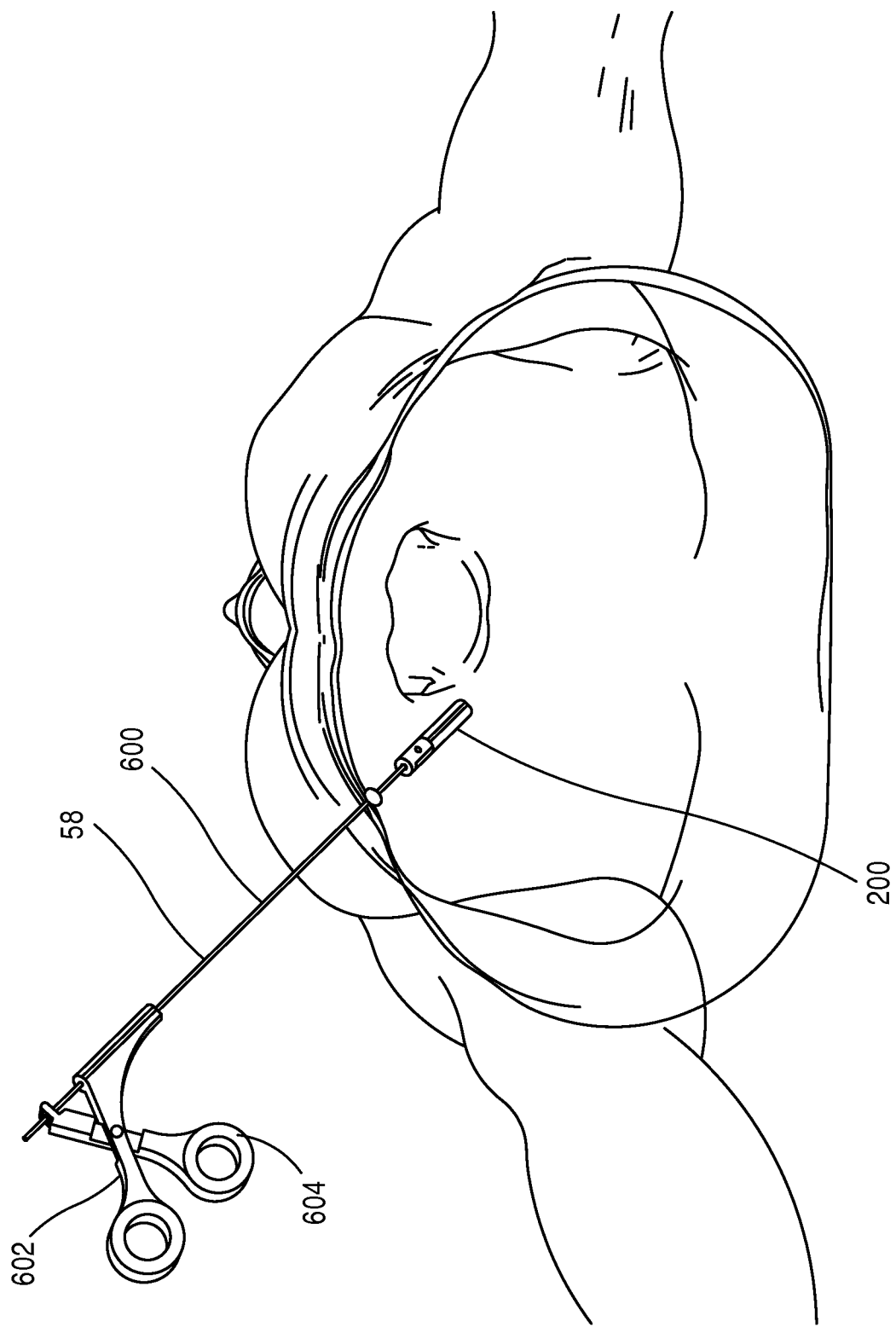
FIGS. 7A-8G are simplified schematics presenting use of a laparoscopic tool with a handle variably positioned with respect to a tool shaft and operable to enhance rigidity by selectively shortening a distal portion of the tool shaft, according to some embodiments of the present invention.
Figure 7B:
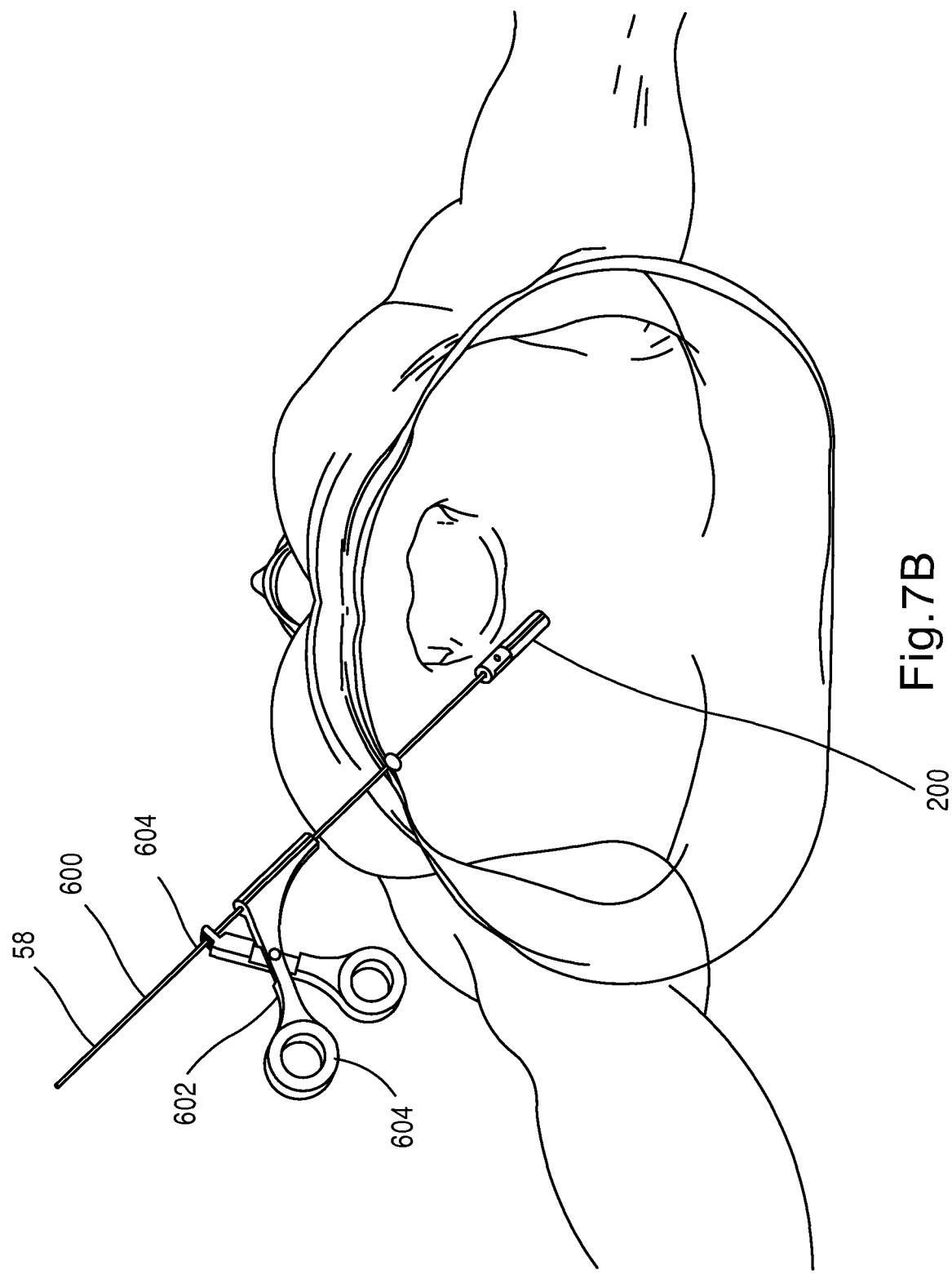

Enhancing Rigidity of a Shaft by Shortening the Shaft: Length-Adjustable Shaft and Handle Attention is now drawn to FIGS. 7A and 7B, which show an embodiment according to the present invention which comprises a laparoscopic tool 58 having a shaft 600 and handle 602 which together comprise a shaft-handle combination 604 in which handle 602 is operable to slide along at least a portion of shaft 600 and to be fixated at a selected position with respect to shaft 600. FIG. 7A shows handle 602 positioned near a proximal end of shaft 600, and FIG. 7B shows handle 602 positioned and fixated closer to a distal end of shaft 600. The effect of positioning handle 602 closer to a distal end of shaft 600 is to position handle 602 closer to a treatment head 200, and to shorten that portion of shaft 600 which connects handle 602 to head 200, thereby enhancing rigidity of that portion of shaft 600. A surgeon may optionally position handle 602 as shown in FIG. 7A, for example while connecting head 200 to shaft 600 by extending shaft 600 through a trocar until it is external to the body, or when manipulating distant tissue, then subsequently position handle as shown in FIG. 7B so as to shorten the effective length of shaft 600, for example to have better control of head 200 while treating closer body tissues.

Additional views of embodiments of tool 58 are provided by FIGS. 8A-8F, according to some embodiments of the present invention. Tool 58 comprises shaft 600 and handle 602, as seen in the figures. In an embodiment shown in these figures shaft 600 comprises an external shaft portion 110 having a lumen and a moveable rod 120 within said lumen, and shaft 600 and handle 602 together comprise a length-adjusting mechanism 604 for adjusting length of that portion of said shaft which extends distally from handle 602. As may be seen when comparing FIG. 8A with FIG. 8B, external shaft portion 110 of shaft 600 is slideable within handle 602. Note the position of proximal end 608 of shaft 600 in the two figures: it may be seen that a portion of shaft 600 which extends distally from handle 602 is longer in FIG. 8A than in FIG. 8B, since a proximal end 608 of shaft 600 is further to the right on FIG. 8A than on FIG. 8B, causing head 200 to be displaced further to the right of the figure also. In other words, head 200 is further distant from handle 602 in FIG. 8A than it is in FIG. 8B.

A knob 606, when somewhat unscrewed, releases shaft 600 which may then 20 slide distally and proximally within handle 602, as shown in the figures. Tightening knob 606 fixes shaft 600 in a user-selected position with respect to handle 602.

Figure 8A:
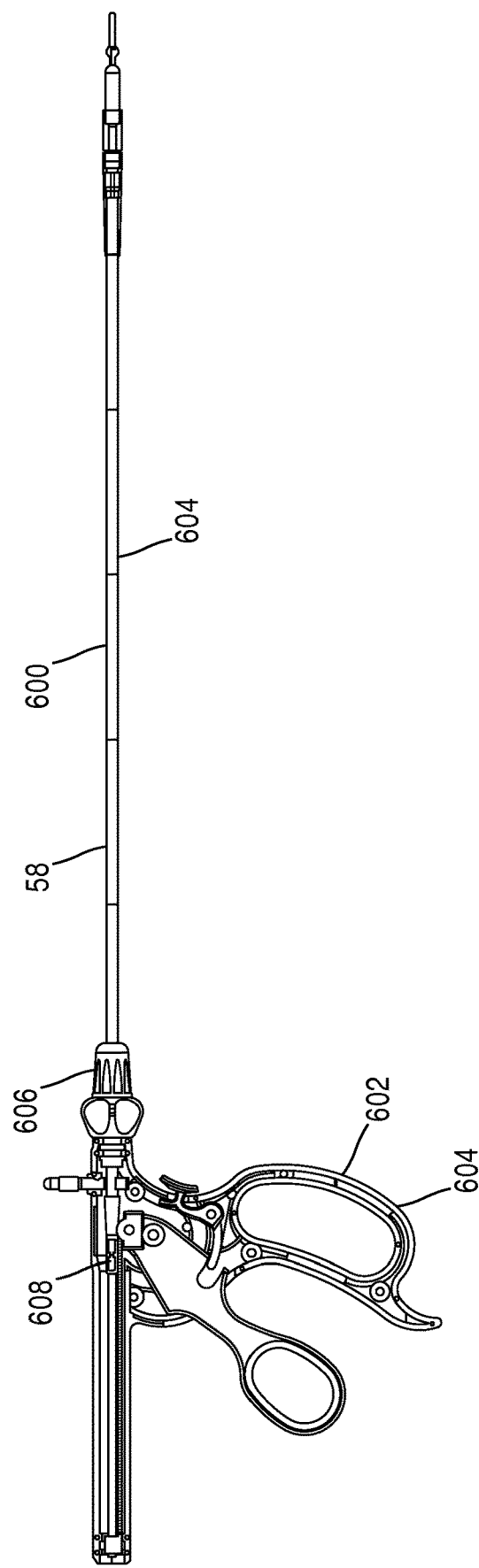
Figure 8B:
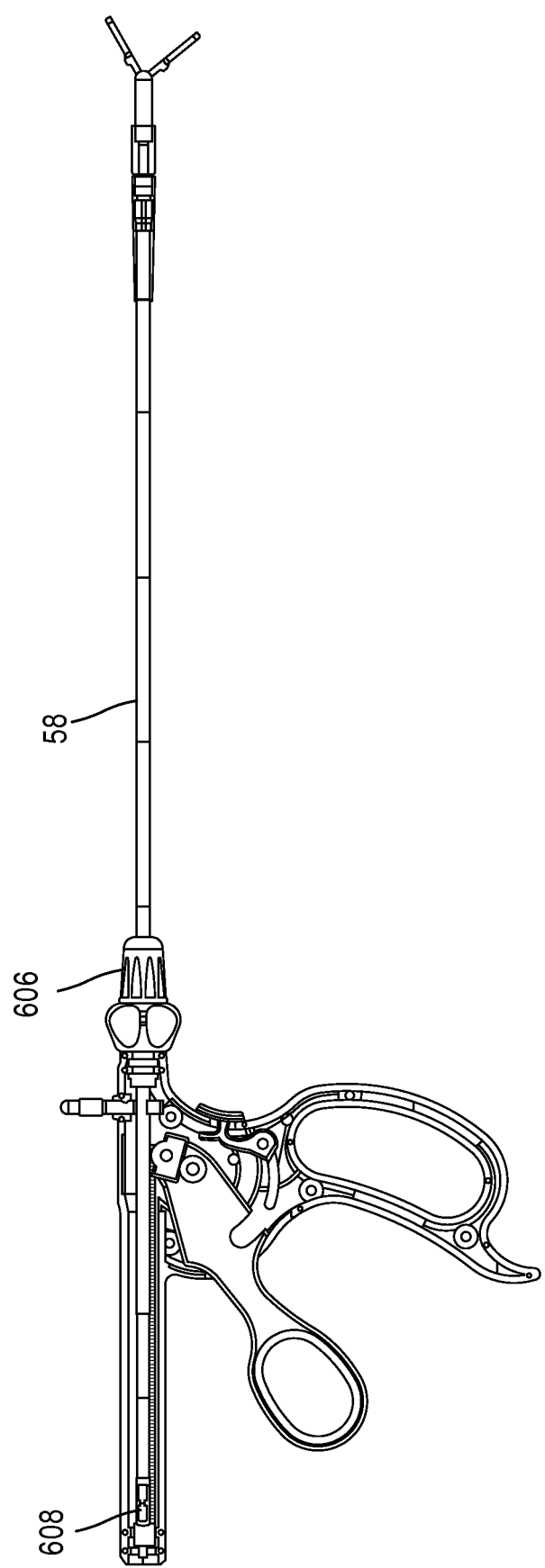
Figure 8C:
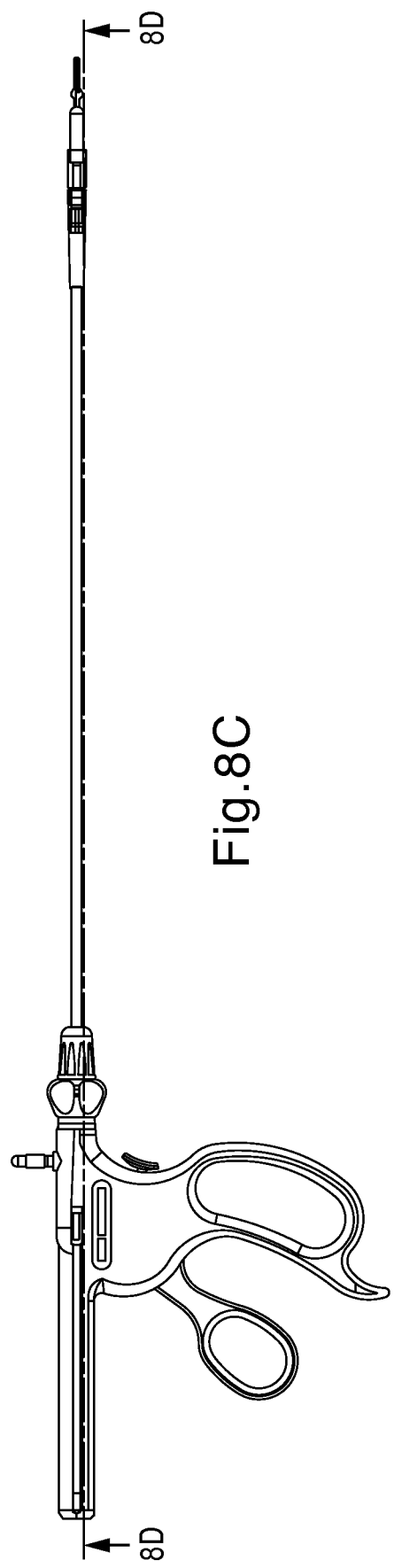
Figure 8D:
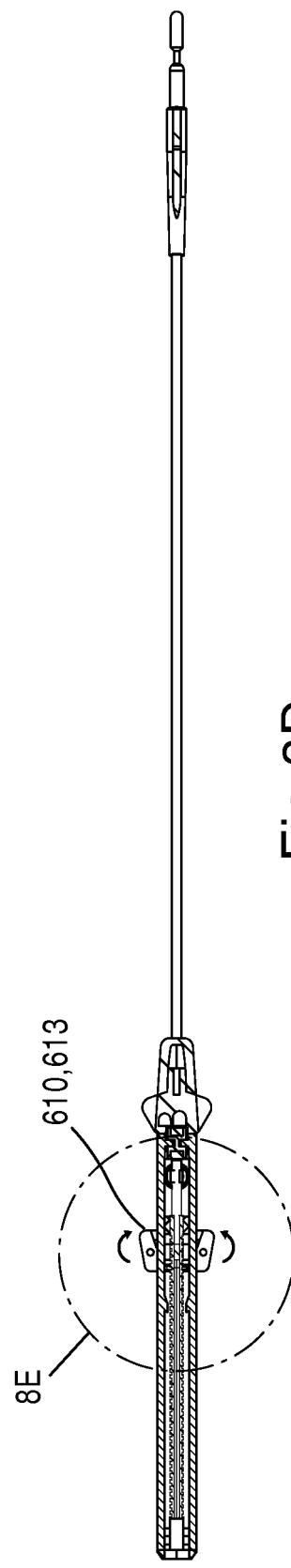
Figure 8F:
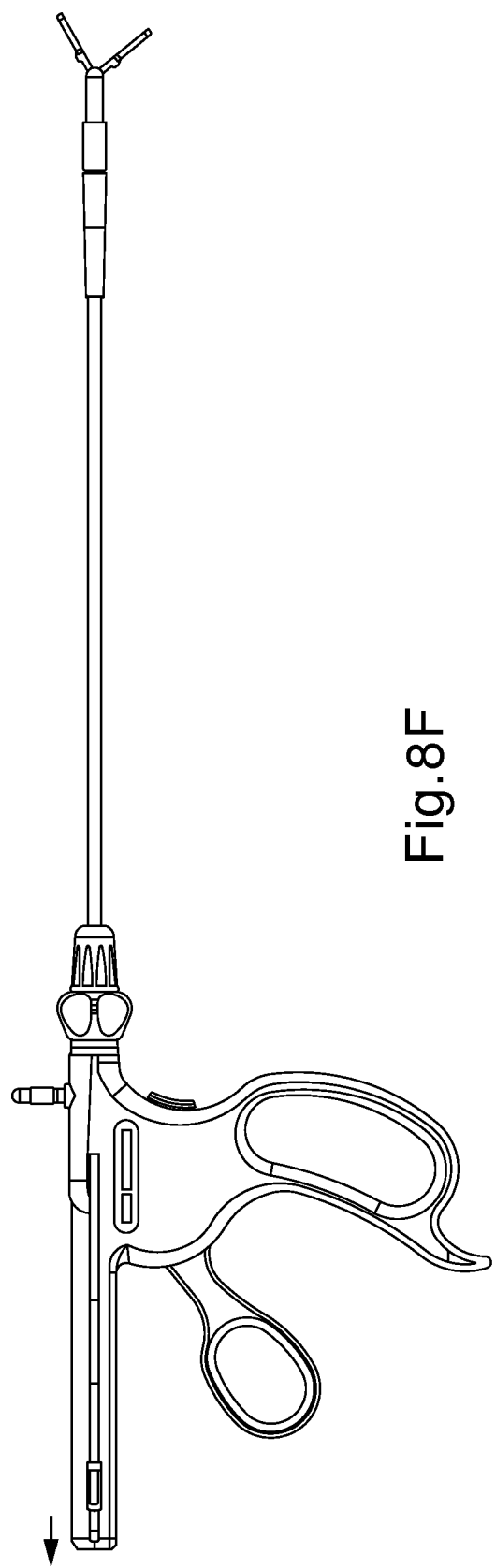

FIGS. 8C and 8F show exemplary dimensions for 'long' and 'short' configurations for an exemplary embodiment of tool 58.

As is well known in laparoscopic tools, head 200 may comprise a plurality of parts which are moveable with respect to each other. Two jaws of an exemplary grasper head 200, for example, are shown closed (near each other) in FIG. 8A and open (far from each other) in FIG. 8B. Control of such treatment heads 200 is typically exercised using a handle such as handle 602 which comprises two independently moveable parts such as finger slot 605 and thumb slot 603 shown in FIGS. 8A and 8B. As is well known in laparoscopic tools, differential movement of moveable parts in a handle such as handle 602 induces differential movement of a rod 120 with respect to an external shaft portion 110, which then induces differential movement of mechanical parts in a treatment head such as head 200, such as in the two grasper jaws shown in closed and open positions in FIGS. 8A and 8B.

Tool 58 consequently requires a mechanism by which handle 602 can induce differential movement of rod 120 with respect to external shaft 110, even though external shaft 110 may be positioned in a variety of positions using knob 606, as explained above. Accordingly, mechanisms are provided for adjusting the positioning of rod 120 with respect to external shaft 110 at whatever position external shaft is set to using knob 606.

Figure 8G:
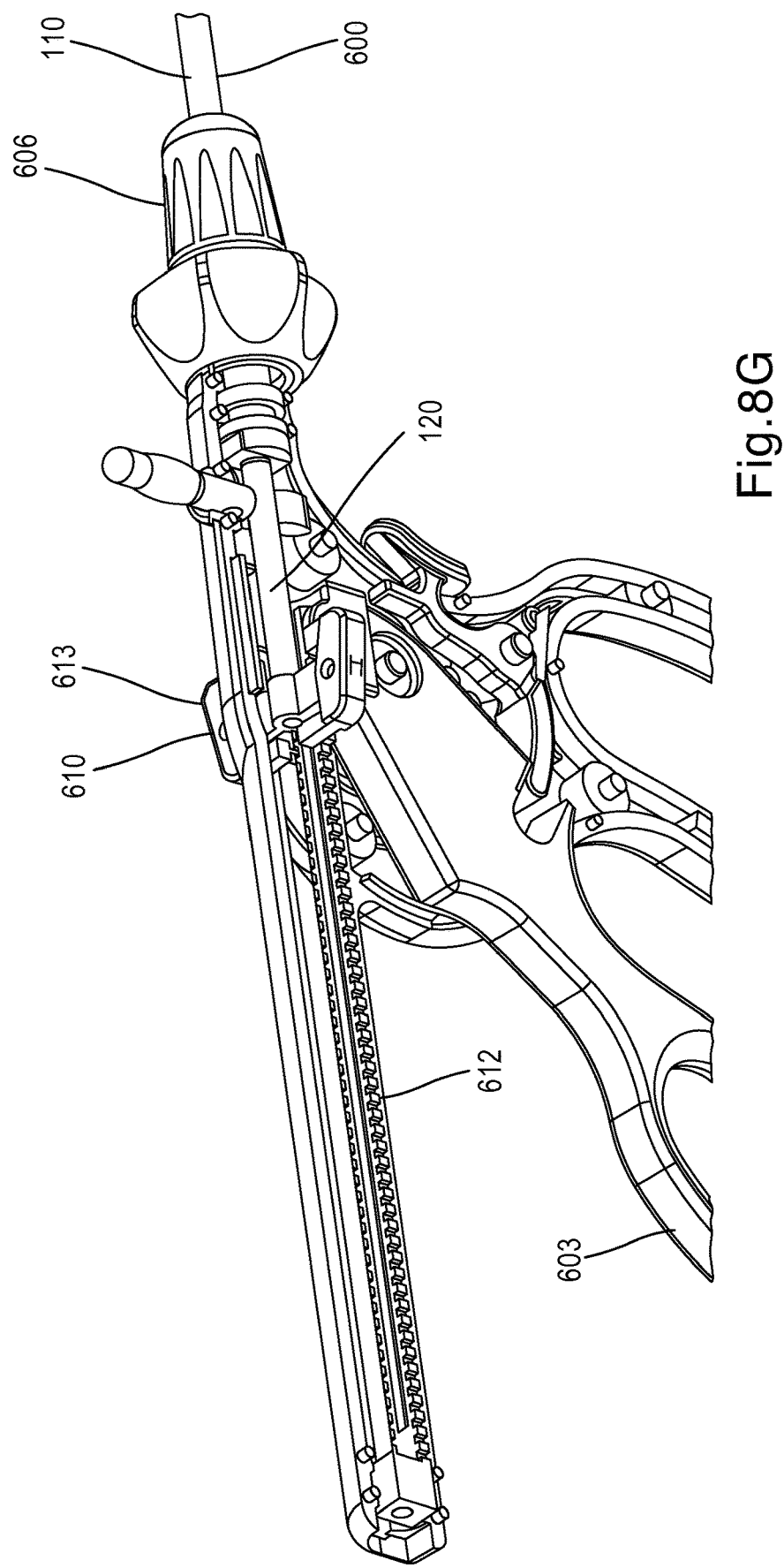

These mechanisms are shown in FIGS. 8E and 8G: in some embodiments handle 602 comprises a bar 612 having spaced teeth or indentations, which bar is mechanically connected to a handle part such as thumb slot 603. Handle 602 further comprises an adjustable rod positioning element 610, which in this exemplary embodiment is a button-controlled rod-connecting element 613 which is slideable along handle 602 when release buttons 611 are pressed.

In some methods of use, shaft external portion 110 is fixed in a user-selected position (i.e. set to a user-selected length) using knob 606, then rod-connecting element 610 is moved so that thumb slot 603 is at a position convenient to the grasp of a surgeon, and release buttons 611 are unpressed, fixing the position of the proximal end of rod 120 with respect to bar 612. Thereafter, movement induced by a surgeon to thumb slot 603 with respect to finger slot 605 will induce a movement in rod 120 with respect to shaft external portion 110, thereby inducing controlled movements in mechanical portions of head 200. Bar 612 and button-controlled rod-connecting element 613 are visible in FIGS. 8D, 8E, and perhaps most clearly in FIG. 8G.

Figure 12:
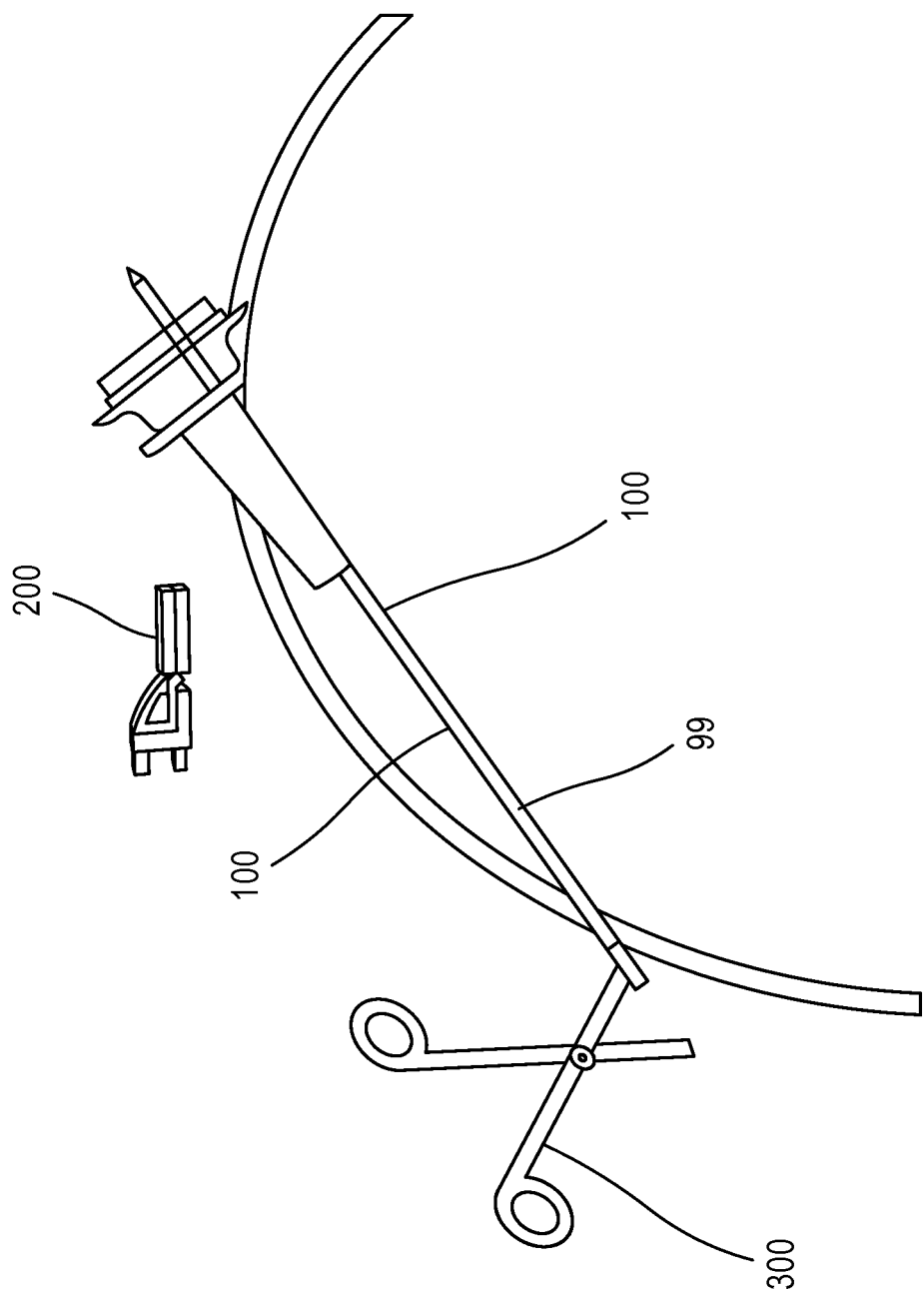
FIG. 12 is a simplified schematic showing a method of laparoscopic surgery disclosed in U.S. Patent Application 2010/0298774 A1.

U.S. Patent Application Publication No. 2010/0298774 A1 and FIG. 12 of the present application which is based thereon show how a shaft, having been introduced into a body cavity, may be caused to extend across a portion of the body cavity, be introduced into a trocar holding an opening in the body cavity, and may optionally be extended through the trocar out of the body cavity, enabling a head 200 to be affixed to a distal end of the shaft outside the body cavity.

In an optional alternative embodiment, a distal portion of the shaft may be introduced into a trocar from within a body cavity, a head 200 may be introduced into the same trocar from outside the body cavity, and head and shaft may be joined within the trocar.

There are several advantages to the latter procedure. In some case, extending shaft beyond the trocar and affixing a head thereto may not be possible or convenient. Additionally, connecting head to shaft within the trocar body is safe because the trocar protects the adjacent tissue.

Laparoscopic Tool with Stiff Rod and Flexible Shaft

U.S. Patent Application Publication No. 2010/0298774 A1 op. cit. teaches methods for fixing and removing an operating head 200 on a distal end of a laparoscopic tool shaft 100 by introducing a distal portion of the shaft into a body cavity (e.g. through a small puncture wound approximately the size of the shaft cross-section), advancing the shaft towards and through a trocar which also penetrates a wall of the body cavity, fixing an operating head 200 on a distal end of the shaft 100 while that distal end extends out of the body cavity through the trocar, then retracting the distal shaft end and operating head into the body cavity for use in treating a tissue. The embodiment presented in FIGS. 9A-9I may in some cases be used to facilitate this and other surgical procedures. FIGS. 9A-9I show views of a laparoscopic tool embodiment which comprises a shaft 709 having a relatively flexible external shaft portion 110, here labeled 710, and a relatively rigid internal rod 120, here labeled 720.

Figure 9A:
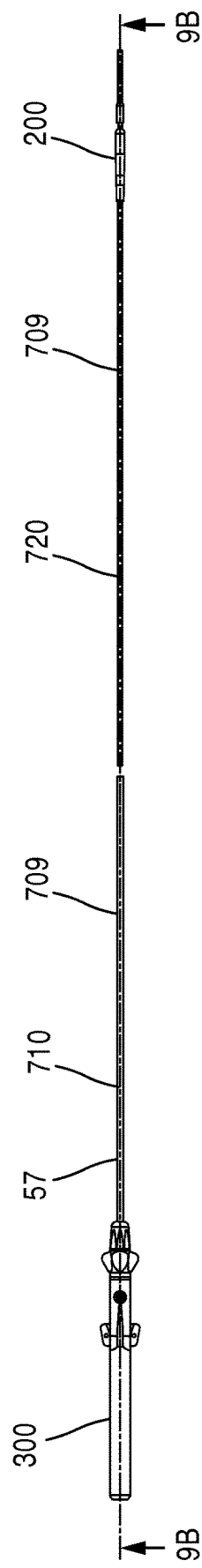
FIGS. 9A-10D are simplified schematics showing laparoscopic tools having flexible external shafts, according to some embodiments of the present invention.
Figure 9B:
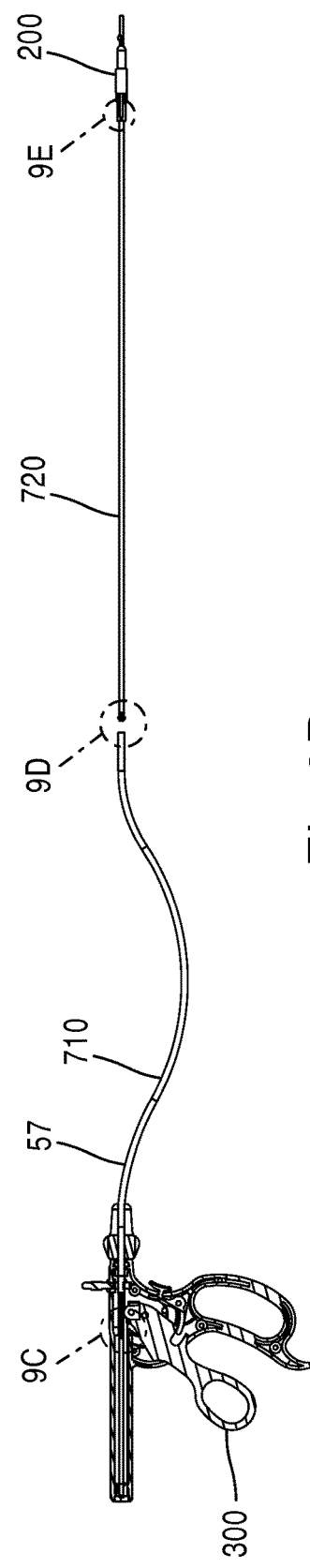
Figure 9E:
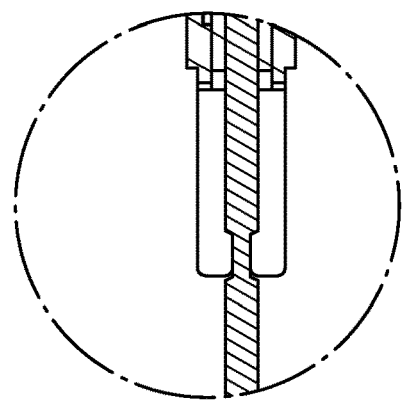
Figure 9D:
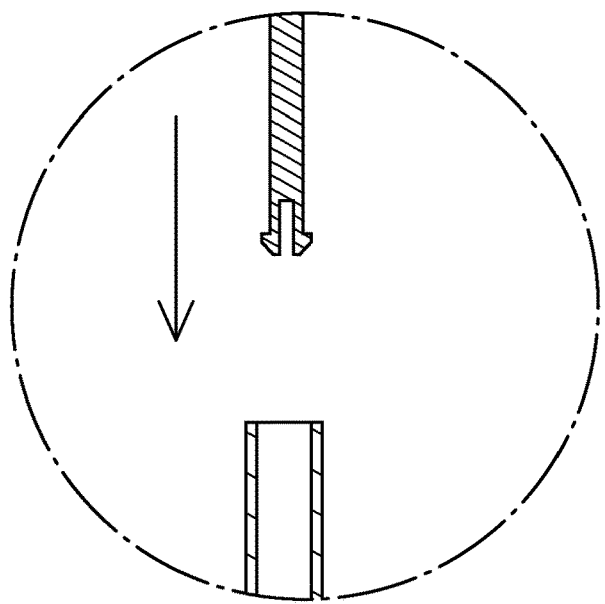
Figure 9C:
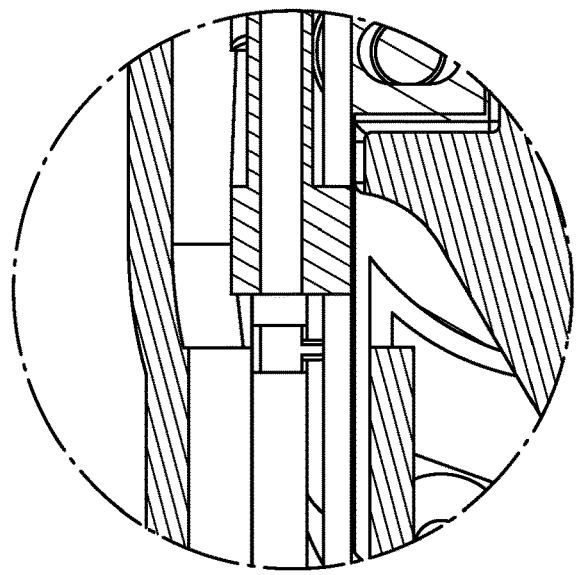
Figure 9I:
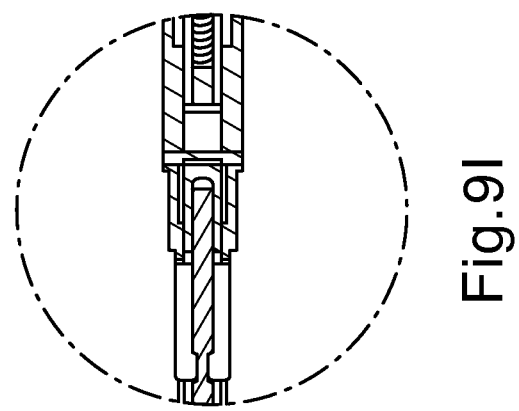
Figure 9H:
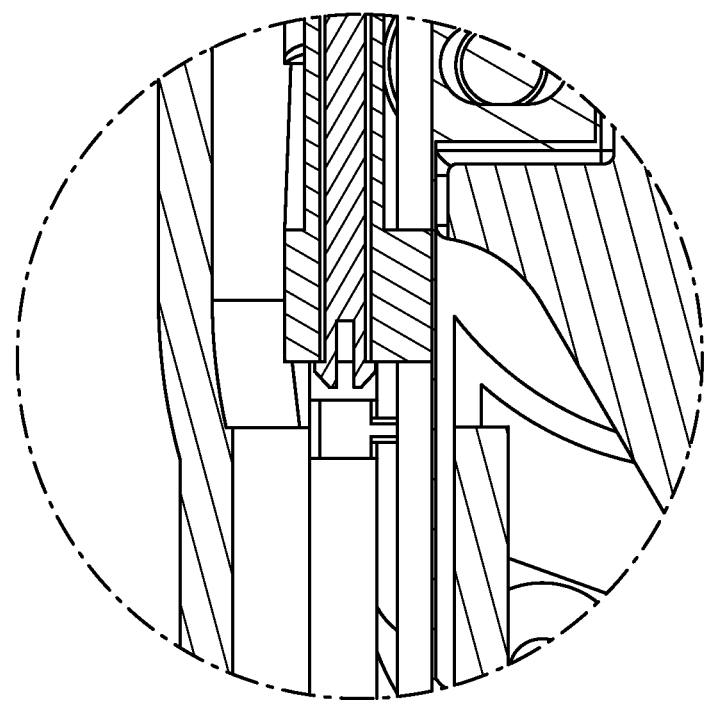

FIGS. 9A and 9F present views from above and FIGS. 9B and 9G present views from the side of a laparoscopic tool 57 having a rigid rod 720 introduceable into a lumen of a flexible external shaft 710. FIGS. 9A and 9B show rod 720 prior to being introduced into external shaft 710, and FIGS. 9F and 9G show tool 57 with rod 720 inserted into external shaft 710. FIGS. 9C, 9D, 9E, 9H and 9I are detailed views of subelements of tool 57 as identified in FIGS. 9A, 9B, 9F and 9G and show optional connecting mechanisms for connecting rod 720 to handle 300 and for connecting external shaft 710 to operating head 200.

Flexible external shaft 710 may be useful in facilitating connection of a head 200 to a shaft 709 through a trocar. In some embodiments head 200 is connected to rod 720 as shown in the figures. A distal portion of flexible shaft 710 is introduced into a body cavity as taught in U.S. Patent Application 2010/0298774 A1. The flexible nature of shaft external portion 710 facilitates the process of introducing shaft external portion 110 into the trocar for passage outside the body. This is useful because in some clinical circumstances the trocar may be so positioned that introducing a straight and rigid shaft 100 therein, from its position where the shaft is inserted into the body cavity from outside the body, would be difficult. For example, this would be the case if the shaft insertion position is relatively close to the trocar position.

Once flexible shaft portion 710 is introduced into the trocar, rigid rod 720 may be introduced into shaft external portion 710, thereby straightening shaft external portion 710 and readying tool 57 for work treating a tissue within the body cavity. In some embodiments, acts may be performed in the following order:

1. Inserting a distal end of a flexible shaft from within a body cavity into a trocar installed in a wall of the body cavity;
2. Connecting a treatment head to a distal end of the flexible shaft;
3. Withdrawing distal end of the flexible shaft and connected treatment head from the trocar into the body cavity;
4. Inserting a relatively rigid rod into the flexible shaft until it approaches the attached treatment head; and
5. Optionally, attaching (docking) the rod's distal end to the treatment head.

In some embodiments, rod 720 bends more than three times as much as external shaft 710, if each is held at a proximal end and an equal force is applied laterally to each distal end. In some embodiments, if rod 720 is held at a proximal end and a lateral force of 80 grams is applied at its distal end, a non-elastic deformation of at least a portion of rod 720 results, whereas if external shaft 710 is held at a proximal end and a lateral force of 80 grams is applied at its distal end, no non-elastic deformation of shaft 710 results.

In some embodiments, external shaft 710 is a tightly-coiled spring-like structure with a helical spring with coils which touch each other when relaxed, and with a hollow lumen between. In some embodiments, external shaft 710 is a metal tube which comprises interlaced non-touching cuttings (e.g. laser cuttings) rendering it flexible. In some embodiments external shaft 710 is covered by a biocompatible thin covering to prevent body tissue from introducing itself between coils of external shaft 710.

In some embodiments, flexible external shaft 710 comprises 'knee' joints, i.e. portions which are relatively more flexible, longitudinally joined to other portions which are relatively less flexible.

Attention is now drawn to FIGS. 10A-10D, which present details and a method of use of some additional embodiments of a laparoscopic tool 59, also comprising a relatively rigid rod used together with a relatively flexible shaft.

Tool 59 differs from tool 57 in that in tool 57 rigid rod 720 is introduced into flexible shaft 710 from a distal end of shaft 710, as described above and shown in FIGS. 9A-9I, however tool 59 is designed so that a relatively rigid rod, here labeled 920 may be introduced into a relatively flexible rod, here labeled 910, from a proximal end of shaft 910, and also optionally through a portion of a handle 300 (optionally a handle 602).

Figure 10A:
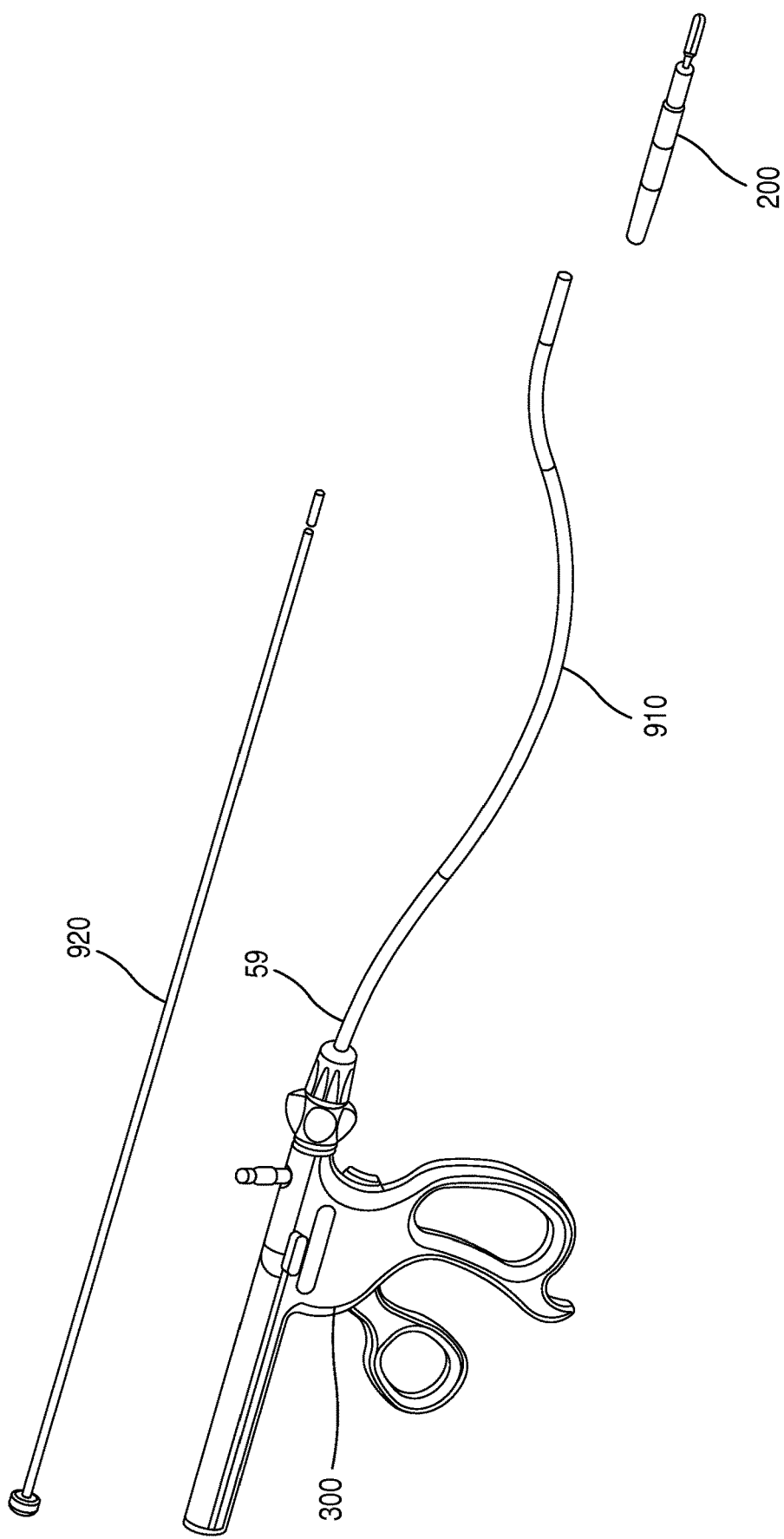

FIG. 10A shows a flexible shaft 910 connected to a handle 300, while treatment head 200 is unconnected and rod 920 is not yet in use.

Figure 10B:
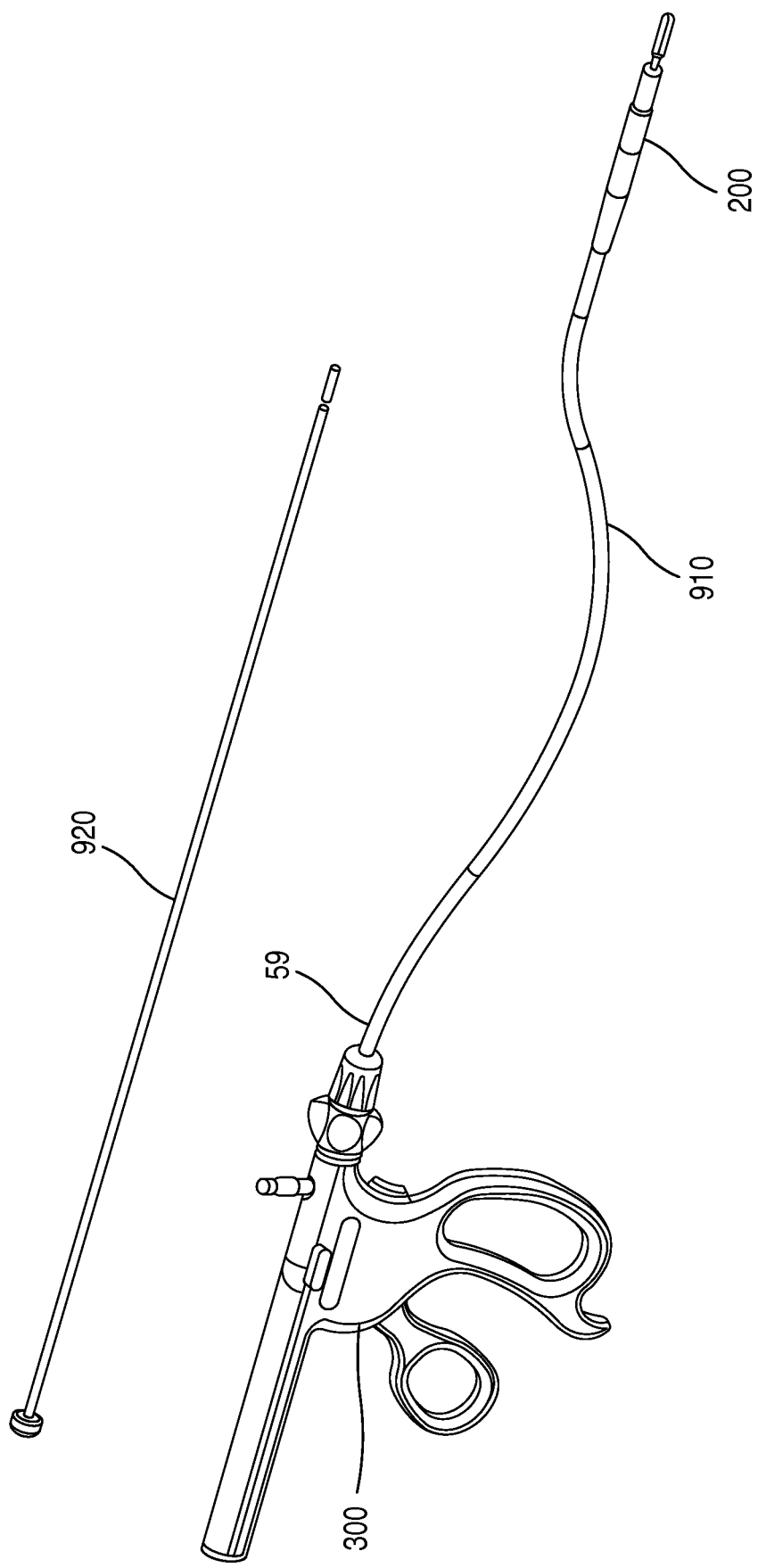

FIG. 10B shows head 200 connected to flexible shaft 910.

Flexibility of shaft 910 may facilitate introducing shaft 910 into a trocar, and will be particularly helpful when the point of introduction of the shaft into the body cavity is relatively near the trocar, since in that circumstance an unbendable shaft might have difficulty be introduced into a trocar which could then be entered only at a very small angle. However, when the distal end of flexible shaft 910 is introduced into the trocar, flexibility of the shaft should make it easier to advance the shaft through the trocar and optionally out of the body. FIG. 10B shows that status of the shaft after this process (or any other process) has enabled a user to affix a head 200 to shaft 910.

Figure 10C:
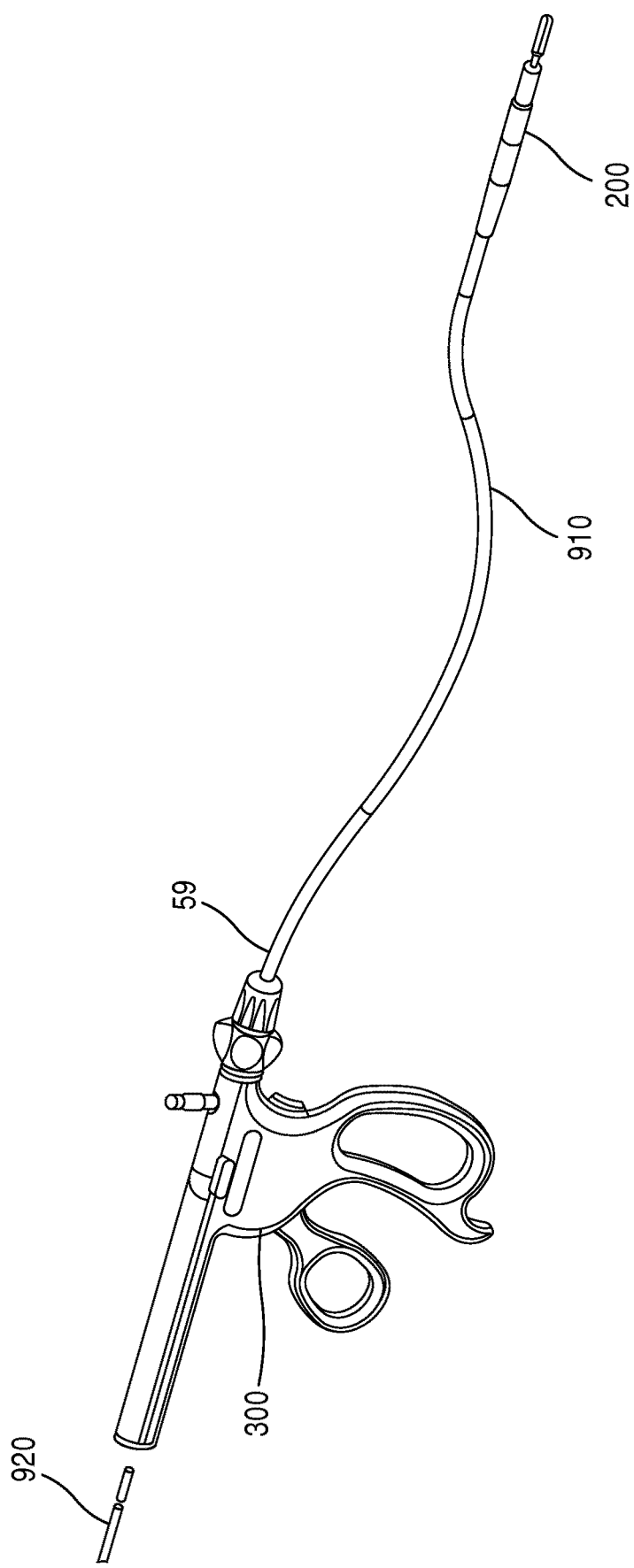
Figure 10D:
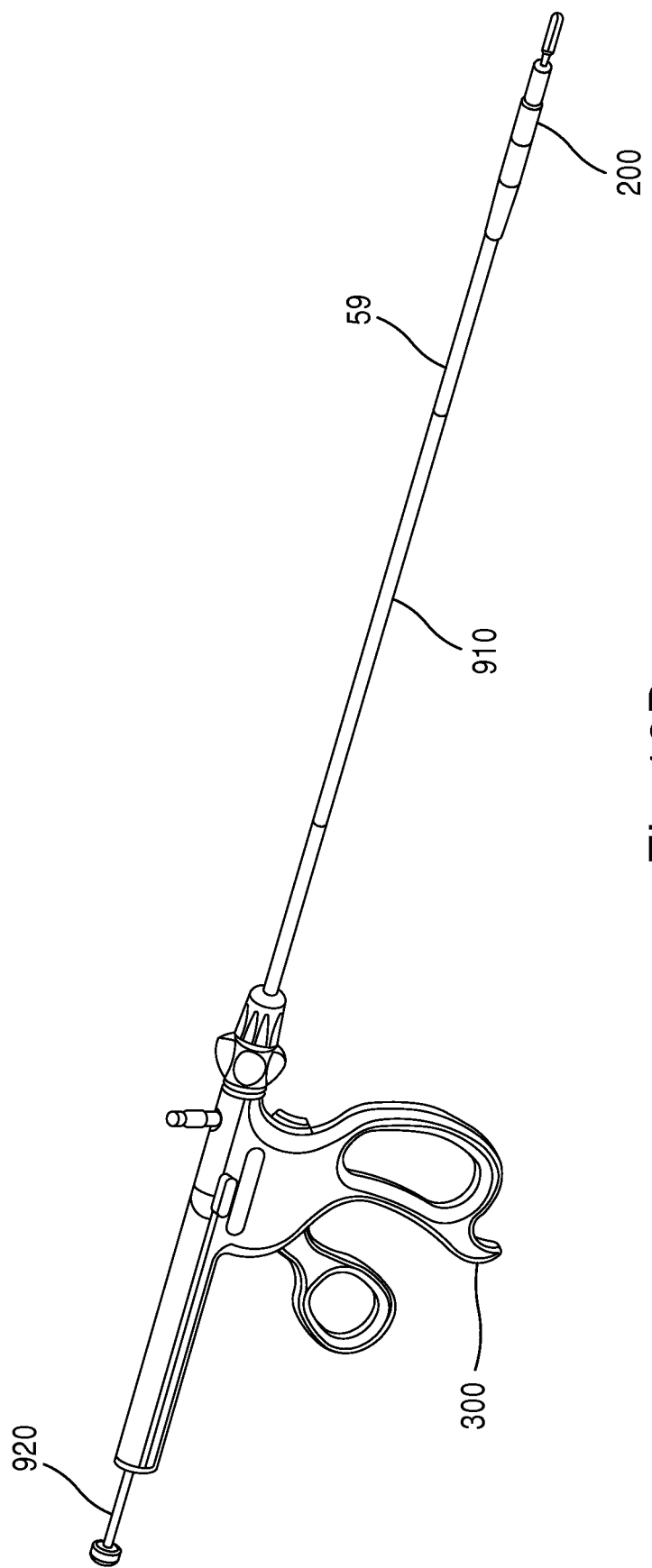

FIG. 10C shows a next stage in a process, where a distal end of a stiff rod 920 is seen approaching handle 300 and shaft 910 from shaft 910's proximal side. FIG. 10D shows a completion of this process, with rod 920 fully inserted and optionally attached to treatment head 200. As may be seen, in some embodiments rigidity of rod 920 imparts a straight and rigid configuration to shaft 910 as well, once rod 920 is introduced therein.

Attention is now drawn to FIGS. 11A-11I, which present a laparoscopic tool 54 which comprises a shaft 1000 which comprises a relatively rigid external shaft portion 1010 and a flexible rod 1020. Flexible rod may optionally be a wire, a guide wire, and/or a braided cable.

Figure 11E:
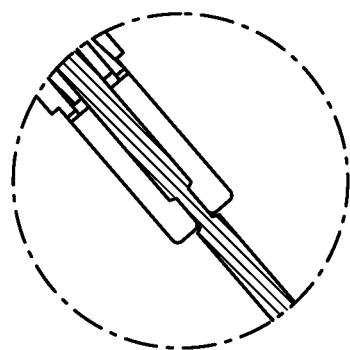
Figure 11D:
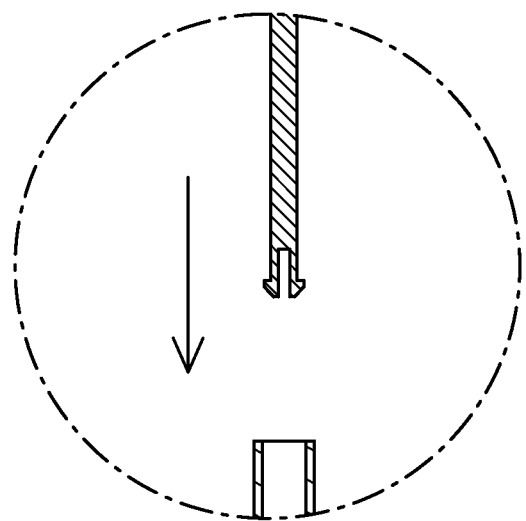
Figure 11C:
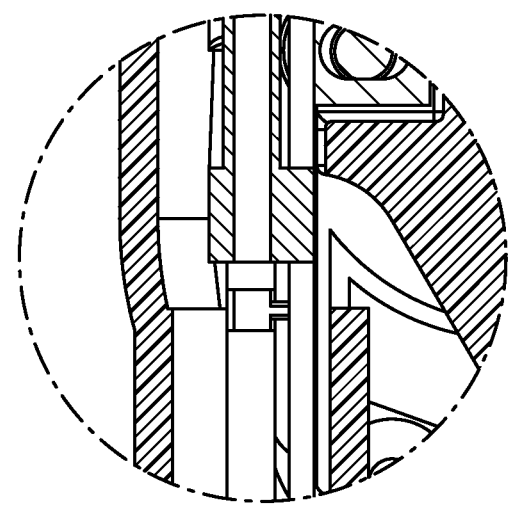
Figure 11I:
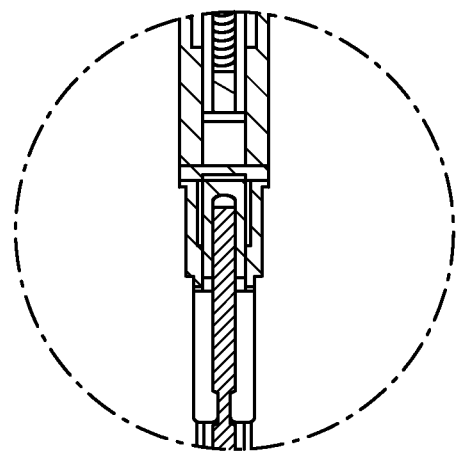
Figure 11H:
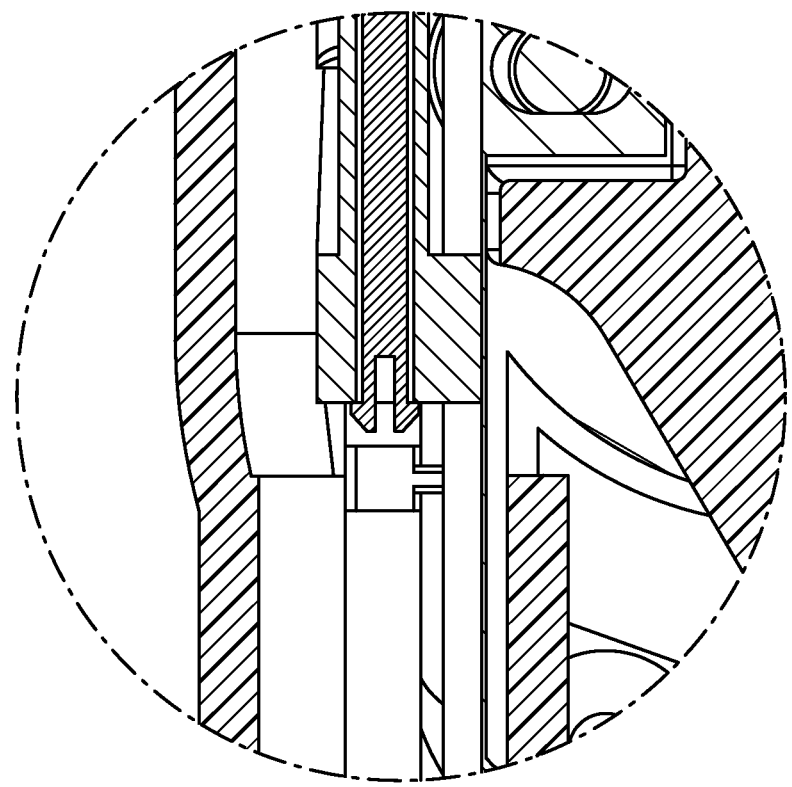

FIGS. 11A and 11F present views from above and FIGS. 11B and 11G present views from the side of laparoscopic tool 54. FIGS. 11A and 11B show flexible rod 1020 prior to being introduced into rigid external shaft 1010, and FIGS. 9F and 9G show tool 54 with rod 1020 inserted into external shaft 1010. FIGS. 11C, 11D, 11E, 11H and 11I are detailed views of subelements of tool 54 as identified in FIGS. 11A, 11B, 11F and 11G and show optional connecting mechanisms for connecting rod 1020 to handle 300 and for connecting external shaft 1010 to an operating head 200 or to an operating head 201, described below.

Flexible rod 1020 may be useful in facilitating connection of a head 200 to a shaft 1000 through a trocar. In some embodiments head 200 is temporarily or permanently connected to rod 1020 as shown in FIGS. 11A and 11B. A distal portion of rigid external shaft portion 1010 is introduced into a body cavity and a distal end of that shaft is caused to approach and optionally to enter a trocar from inside the body cavity. Rod 1020 attached to head 200 or to a head 201. The flexible nature of rod 1020 facilitates the process of introducing rod 1020 into shaft external portion 1010, even though they may not initially be well aligned with each other. For example, rod 1020 connected to a head 200 or 201 maybe be introduced rod-first into a body cavity through a trocar, and threaded into shaft 1010 until rod 1020 connects to a handle 300 and shaft 1010 connects to head 200/201. This threading process can begin outside the body (if a distal end of external shaft 1010 extends through the trocar and to a position outside the body), or inside the body cavity (if rod 1020 extends into the body cavity through the trocar), or rod 1020 and external shaft 1010 may meet within the trocar body. These procedures are particularly useful if the trocar is so positioned that extending a straight and rigid shaft from a position where it is desired to introduce it into a body cavity makes it difficult to pass it easily outside the body through an adjacent trocar. For example, this would be the case if the shaft insertion position is relatively close to the trocar position.

In an alternative embodiment the rod can be threaded from the shafts proximal side through the shaft distal end and through the port out of the body. This can be possible due to the flexible nature of the rod. Then the surgeon can connect manually the head to the flexible rod distal end and afterwards pull the rod/wire/guide wire and connect/dock the head to the shaft.

In some embodiments, rod 1020 is more than three times as flexible as external shaft 1010, as measured by how much rod 1020 and external shaft 1010 bend if equal bending forces are applied to equal lengths of each.

Figure 11J:
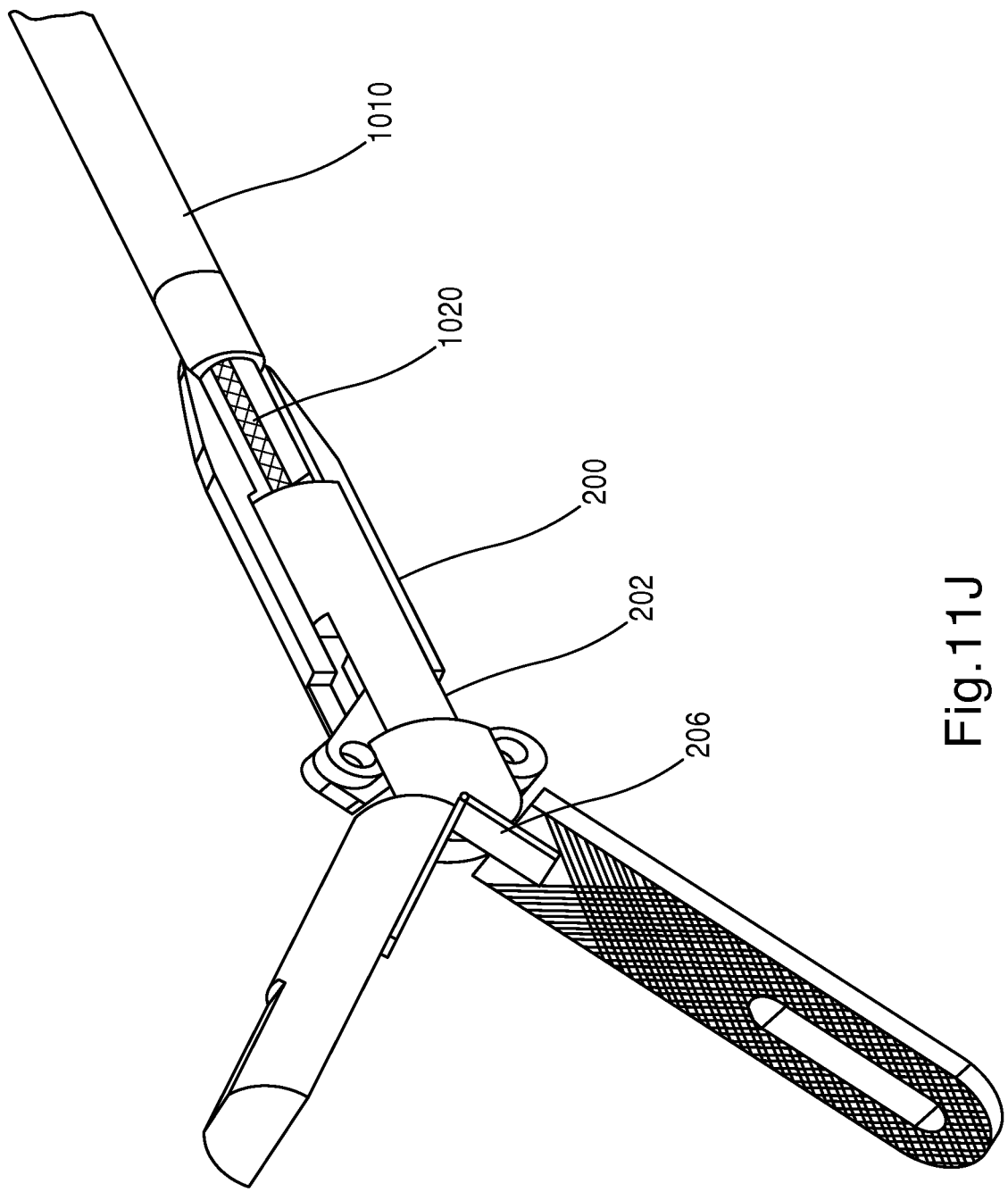

Attention is now drawn to FIG. 11J, which presents a treatment head 201 which comprises a spring 206. An exemplary and non-limiting embodiment of spring 206 is shown in the figure. Rod 1020, being flexible and optionally being implemented as a wire or cable, is generally better adapted to transferring motion by pulling than by pushing. Accordingly, in some embodiments tool 54 comprises a head 201 in which a spring such as spring 206 serves to keep a mechanism of head 201 in a default configuration. For example, in an exemplary embodiment shown in FIG. 11J, head 201 is a grasper with a "normally open" configuration, which can be closed by pulling on rod 1020, but opens of itself when a surgeon ceases to pull on rod 1020. In an alternative example of a head 201 (not shown), a dissector may be provided with a spring which closes the head, and manually pulling on rod 1020 opens it. Head 201 is therefore well adapted for use with a flexible rod 1020 which optionally is used only to pull and not to push.

As used herein the term "about" refers to ±10%.

The terms "comprises", "comprising", "includes", "including", "having" and their conjugates mean "including but not limited to".

The term "consisting of" means "including and limited to".

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Attention is now directed to the examples provided as Appendix A and Appendix B attached hereto. These Appendices are an integral part of this specification. The examples provided in these appendices, together with the above descriptions, illustrate some embodiments of the invention in a non limiting fashion.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A laparoscopic tool comprising:
   a shaft including an external shaft portion defining a lumen and a rod movable within said lumen, the rod being permanently connected or detachably connectable to a laparoscopic tool head;
   a handle having differentially moveable parts to actuate the laparoscopic tool head via the rod, the handle being attachable to said rod at a plurality of user-selected positions, the handle comprising a tooth bar having a plurality of teeth spaced along a longitudinal axis of the handle; and
   a user-controllable movable element configured to slide relative to the tooth bar to move said rod with respect to said external shaft portion and to fix a position of a proximal end of said rod relative to the handle.

2. The laparoscopic tool of claim 1, wherein said external shaft portion is slideable within said handle and fixable at a plurality of user-selected positions with respect to said handle via a rotatable knob secured to a distal end of said handle.

3. The laparoscopic tool of claim 1, wherein the shaft further comprises an electrically insulating layer between said rod and said external shaft portion.

4. The laparoscopic tool of claim 1, further comprising a sheath sized and shaped to cover at least a part of the shaft and sufficiently rigid to impede bending of the part of the shaft when said part of the shaft is covered by the sheath.

5. The laparoscopic tool of claim 4, wherein the sheath is embodied as an extension of the laparoscopic tool head.

6. The laparoscopic tool of claim 4, wherein the sheath is an extension of the handle.

7. The laparoscopic tool of claim 4, wherein the sheath comprises a connection mechanism for connecting the sheath to the handle.

8. The laparoscopic tool of claim 4, wherein the sheath is sterilized for insertion into a body cavity and sized and shaped to cover at least part of a distal portion of the shaft when said distal shaft portion is within a body cavity.

9. The laparoscopic tool of claim 1, wherein the user-controllable movable element includes two release buttons slidably mounted on opposite sides of the handle.

10. The laparoscopic tool of claim 1, wherein the user-controllable movable element is configured to engage the plurality of teeth to fix the position of the proximal end of the rod relative to the handle.

11. The laparoscopic tool of claim 1, further comprising the laparoscopic tool head attached to a distal end of the shaft.

12. The laparoscopic tool of claim 1, wherein the user-controllable movable element further comprises at least one release button that is pivotably mounted to permit the user-controllable movable element to slide relative to the tooth bar when depressed.

\* \* \* \* \*